United States Patent [19]

Burkhard et al.

[11] 3,998,803
[45] Dec. 21, 1976

[54] 5-ARYLAZO-6-HYDROXY-PYRIDONE-2 DYES CONTAINING AN AMINO OR SUBSTITUTED AMINO GROUP

[75] Inventors: Hermann Burkhard, Neu-Allschwil; Roland Entschel; Willy Steinemann, both of Basel, all of Switzerland

[73] Assignee: Fidelity Union Trust Company, Executive Trustee Under the Sandoz Trust, Newark, N.J.

[22] Filed: June 17, 1974

[21] Appl. No.: 480,092

Related U.S. Application Data

[60] Division of Ser. No. 337,167, March 1, 1973, which is a continuation-in-part of Ser. No. 824,297, May 13, 1969, abandoned.

[30] Foreign Application Priority Data

July 25, 1968 Switzerland ............... 11195/68
July 13, 1968 Switzerland ............... 16898/68
July 26, 1968 Switzerland ............... 17580/68

[52] U.S. Cl. .................. 260/156; 260/154; 260/155; 260/294.9; 260/295 AM
[51] Int. Cl.² ............... C09B 29/36; C09B 31/14; D06P 1/08; D06P 3/70
[58] Field of Search ............. 260/156, 155, 154

[56] References Cited

UNITED STATES PATENTS 2,431,190  11/1947  Morgan ................. 260/156 X
3,487,066  12/1969  Ritter et al. ............. 260/156

*Primary Examiner*—Floyd D. Higel
*Attorney, Agent, or Firm*—Gerald D. Sharkin; Richard E. Vila; Melvyn M. Kassenoff

[57] ABSTRACT

Dyes of the formula

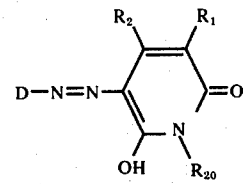

wherein
$R_1$ is hydrogen or cyano,
$R_2$ is alkyl, aryl or heterocyclyl, or a substituted derivative thereof,
$R_{20}$ is hydrocarbyl, heterocyclyl or amino, or a substituted derivative thereof preferably containing a protonizable nitrogen atom, and
D is aromatic carbocyclyl or heterocyclyl, or a substituted derivative thereof, with the proviso that it is free of cationic groups, with the proviso that the molecule contains at least one protonizable nitrogen atom. These dyes are eminently suitable for the dyeing and printing of textiles which consist of or contain fibers of polyacrylonitrile or copolymers of acrylonitrile. They are suitable for dyeing polyesters and polyamides modified to contain acid groups as well as leather and paper. The dyes have high tinctorial strengths and give level dyeings exhibiting good fastness to light and wet treatments. The dyes are produced by diazotizing an amine of the formula $D-NH_2$ and coupling the resulting compound with a pyridone of the formula

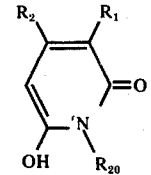

18 Claims, No Drawings

5-ARYLAZO-6-HYDROXY-PYRIDONE-2 DYES CONTAINING AN AMINO OR SUBSTITUTED AMINO GROUP

This application is a division of application Ser. No. 337,167, filed Mar. 1, 1973, which is a continuation-in-part of application Ser. No. 824,297, filed May 13, 1969 and now abandoned.

The dyes of this invention have the formula

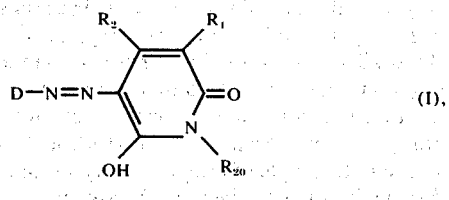

wherein

D is carbocyclic aryl or heterocyclic aryl which may be substituted but is free of cationic groups, $R_1$ is hydrogen or cyano, $R_2$ is alkyl, aryl or heterocyclyl which may be substituted, and $R_{20}$ is hydrocarbyl which may be substituted, heterocyclyl which may be substituted or amino which may be substituted, and each of these radicals bears a protonizable N atom.

More particularly, the dyes have the formula

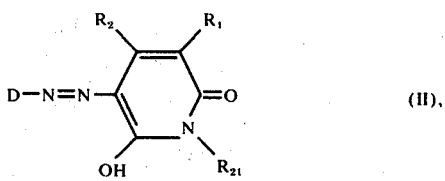

wherein $R_{21}$ is

wherein each of $R_{22}$ and $R_{23}$ is independently hydrogen or optionally substituted hydrocarbyl or $R_{22}$ and $R_{23}$ taken together and with the nitrogen to which they are joined are heterocyclyl (e.g., a pyrrolidine, piperidine, morpholine, aziridine or piperazine ring), $X_1$ is alkylene which may be substituted and may be interrupted by hetero atoms, $X_2$ is a direct link or a divalent bridge member, $X_3$ is a nitrogen or carbon atom,

is a saturated or partially saturated, optionally substituted multimembered ring, e.g., a five- or six-membered ring, $Y_2$ is a radial containing a protonizable nitrogen atom, Ring B may be further substituted, and $R_1$, $R_2$ and D are as defined above.

Particularly good dyes are those wherein $R_1$ is cyano as well as those wherein $R_2$ is alkyl or phenyl and particularly those wherein $R_1$ is cyano and $R_2$ is alkyl or phenyl.

Throughout the specification and claims, halo is preferably chloro, bromo or fluoro.

Examples of hydrocarbyl radicals are optionally substituted alkyl radicals (including cycloalkyl radicals) and optionally substituted aryl radicals, e.g., cyclohexyl, alkylcyclohexyl and phenyl radicals.

Alkyl radicals are straight or branched and generally contain 1 to 12 or 1 to 6 carbon atoms and preferably 1, 2, 3 or 4 carbon atoms, i.e., they are preferably lower alkyl radicals. The substituents of substituted alkyl radicals are halo atoms and hydroxy, cyano, protonizable amino group-containing and aryl (e.g. phenyl) groups. Where the substituent of substituted alkyl is aryl, substituted alkyl is an aralkyl group e.g., benzyl. Alkoxy radicals contain 1 to 6 and preferably 1, 2 or 3 carbon atoms.

All of the aryl radicals (including the carbocyclic aryl and heterocyclic aryl radicals, e.g., phenyl, naphthyl, tetrahydronaphthyl, pyridyl, quinolyl and tetrahydroquinolyl radicals) may be substituted, particularly by non-water solubilizing substituents, e.g., halo, nitro, cyano, thiocyano, hydroxy, alkyl, alkoxy, trifluoroalkyl, trichloroalkyl, phenyl, phenoxy, amino, alkylamino, dialkylamino, anilino, acyl, acyloxy, acylamino (e.g., urethane, alkylsulfonyl, arylsulfonyl, sulfamoyl, alkylsulfamoyl, dialkylsulfamoyl and arylsulfamoyl) and arylazo (e.g., phenylazo, diphenylazo and naphthylazo).

The protonizable groups are groups that contain a nitrogen atom which, in acid medium, and particularly in a mineral acid medium, add on a proton, i.e., which form salts with the addition of a proton. In this context, protonizability is the capacity of a nitrogen atom to add a proton, e.g., that of a mineral acid such as hydrochloric acid, so as to render the dye water-soluble.

The heterocyclic radicals and the groups of the formula

are, for example, radicals of saturated or unsaturated, optionally substituted multimembered rings, preferably 5- or 6-membered rings, on which further cycloaliphatic, heterocyclic or aromatic rings may be condensed, e.g., pyridine, quinoline, piperidine, pyrrolidine, morpholine, aziridine, piperazine, isoquinoline, tetrahydroquinoline, pyrazole, triazole, pyridazine, imidazole, pyrimidine, thiazole, benzothiazole, thiadiazole, indazole, pyrrole, indole, oxazole, isoxazole, pyrazoline and tetrazole rings.

Examples of $R_{20}$ are radicals of the formulae

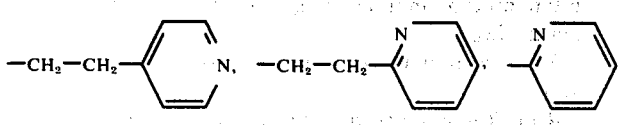

The optionally substituted amino group may be a primary, secondary or tertiary amino group. Examples of substituents on the amino group are alkyl, aralkyl, cycloalkyl and aryl radicals such as phenyl radicals.

The divalent bridge members $X_1$ and $X_2$ may be, for example, substituted alkylene radicals or alkylene radicals having 1 to 12 or preferably 1 to 6 carbon atoms. These radicals may be straight or branched and may be attached to ring members or interrupted by ring members, e.g., cyclohexylene and phenylene radicals, or hetero atoms or groups of hetero atoms, e.g., —O—, —S—,

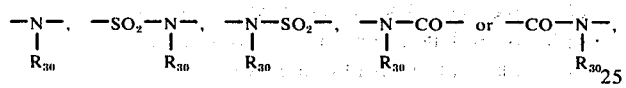

wherein $R_{30}$ is hydrogen or an optionally substituted hydrocarbyl radical.

The divalent bridge members are preferably bound through a carbon atom to the N atom capable of adding on a proton. Examples of bridge members are —CO—, —SO$_2$—, —(CH$_2$)$_p$—,

—O—(CH$_2$)$_p$—, —(CH$_2$)$_p$—O—(CH$_2$)$_q$—, —CH$_2$—CHOH—CH$_2$—, —CH$_2$—NH—CO—CH$_2$—, —CH$_2$—CO—NH—CH$_2$—, —(CH$_2$)$_p$—NH—(CH$_2$)$_q$—, —(CH$_2$)$_q$—CO—, —CO—(CH$_2$)$_q$—, —N-H—CO—(CH$_2$)$_q$—,

and —NH—CH$_2$—CHOH—CH$_2$— wherein $p$ is 1 to 6, $q$ is 1 to 6 and $R_{30}$ is as defined above.

More particularly the compounds of this invention have the formula

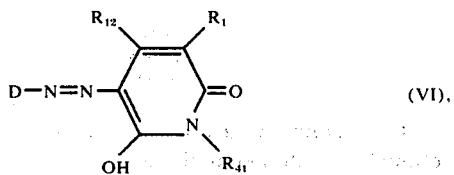

wherein

D is carbocyclic aryl, substituted carbocyclic aryl, heterocyclic aryl or substituted heterocyclic aryl, wherein carbocyclic aryl is phenyl, naphthyl or tetrahydronaphthyl, heterocyclic aryl is pyridyl, quinolyl, tetrahydroquinolyl, 1,2,4-triazolonyl, 1,2,4-triazolyl, indazolyl, thiadiazolyl, thiazolyl or benzothiazolyl, and each substituent of substituted carbocyclic aryl and substituted heterocyclic aryl is independently halo, nitro, cyano, thiocyano, hydroxy, alkyl, alkoxy, trifluoroalkyl, trichloroalkyl, phenyl, phenoxy, chlorophenoxy, amino, alkylamino, dialkylamino, anilino, 2,4-dinitroanilino, acyl, acyloxy, acylamino (e.g., carbamyl, phenylcarbamoyl, alkylsulfonyl, arylsulfonyl, sulfamoyl, alkylsulfamoyl, dialkylsulfamoyl, arylsulfamoyl, N-alkyl-N-phenylsulfamoyl, alkylcarbonyl, alkoxycarbonyl, alkylcarbonylamino, benzamido and alkylbenzoyl), phenylazo, diphenylazo or naphthylazo, $R_1$ is hydrogen or cyano, $R_{12}$ is alkyl, phenyl or benzyl, $R_{41}$ is

or

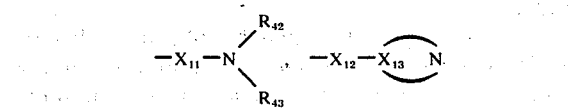

wherein each of $R_{42}$ and $R_{43}$ is independently hydrogen, alkyl, substituted alkyl, cyclohexyl, alkylcyclohexyl, carbocyclic aryl or substituted carbocyclic aryl, wherein each substituent of substituted alkyl is independently hydroxy, chloro or cyano, carbocyclic aryl is phenyl, naphthyl or tetrahydronaphthyl and each substituent of substituted carbocyclic aryl is independently halo, nitro, cyano, thiocyano, hydroxy, alkyl, alkoxy, trifluoroalkyl, trichloroalkyl, phenyl, phenoxy, amino, alkylamino, dialkylamino, anilino, acyl, acyloxy, acylamino, (e.g., carbamyl groups, alkylsulfonyl, arylsulfonyl, sulfamoyl, alkylsulfamoyl, dialkylsulfamoyl and arylsulfamoyl), phenylazo, diphenylazo or naphthylazo, or $R_{42}$ and $R_{43}$ taken together and with the nitrogen to which they are joined form a piperidinyl, pyrrolidinyl, morpholinyl, aziridinyl or piperazinyl ring, $X_{11}$ is —Alk—, —Z—Alk—, —Alk—Z— or —Alk'—Z—Alk'— wherein Alk is straight or branched chain alkylene of 1 to 12 carbon atoms or straight or branched chain alkylene of 1 to 12 carbon atoms substituted by halo, hydroxy, cyano, phenyl, dialkylamino or piperidino, each —Alk'— is independently straight or branched chain alkylene or straight or branched chain alkylene substituted by halo, hydroxy, cyano, phenyl, dialkylamino or piperidino, with the proviso that the two —Alk'— radicals together contain 2 to 12 carbon atoms, and Z is

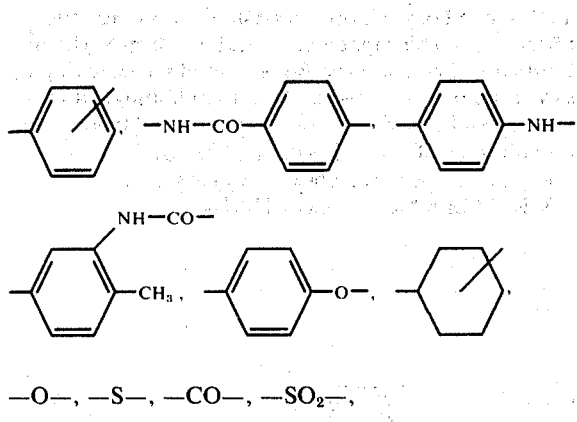

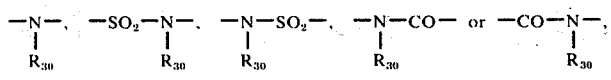

wherein R₃₀ is hydrogen, alkyl, substituted alkyl, cyclohexyl, alkylcyclohexyl, carbocyclic aryl or substituted carbocyclic aryl, wherein each substituent of substituted alkyl is independently chloro, hydroxy or cyano, each carbocyclic aryl is independently phenyl, naphthyl or tetrahydronaphthyl and each substituent of substituted carbocyclic aryl is independently halo, nitro, cyano, thiocyano, hydroxy, alkoxy, alkyl, trifluoroalkyl, trichloroalkyl, phenyl, phenoxy, amino, alkylamino, dialkylamino, anilino, acyl, acyloxy, acylamino (e.g., carbamyl groups, alkylsulfonyl, arylsulfonyl, sulfamoyl, alkylsulfamoyl, dialkylsulfamoyl and arysulfamoyl), phenylazo, diphenylazo or naphthylazo, $X_{12}$ is a direct link or $X_{11}$, $X_{13}$ is a carbon or nitrogen atom, and

is a pyridine, piperidine, pyrrolidine, morpholine, aziridine, piperazine or pyrazoline ring or amidino, wherein each alkyl and alkyl radical of each trifluoroalkyl, trichloroalkyl, alkylamino, dialkylamino, alkylsulfonyl, alkylsulfamoyl, dialkylsulfamoyl, N-alkyl-N-phenylsulfamoyl, alkylcarbonyl, alkylcarbonylamino, alkylbenzoyl, substituted alkyl and alkylcyclohexyl independently contains 1 to 12 carbon atoms, and preferably 1, 2, 3 or 4 carbon atoms, and each alkoxy and alkoxy radical of alkoxycarbonyl independently contains 1 to 6 carbon atoms.

More preferred are the compounds of the formula $$\text{(VII)}$$

wherein

D' is phenyl, substituted phenyl, thiazolyl, 1,2,4-triazolonyl, lower alkyl-1,2,4-triazolyl, indazolyl, lower alkylindazolyl, 1,3,4-thiadiazolyl, lower alkyl-1,3,4-thiadiazolyl or lower alkylsulfonylbenzothiazolyl, wherein each substituent of substituted phenyl is independently chloro, bromo, nitro, cyano, lower alkyl, phenyl, lower alkoxy, phenoxy, 4-chlorophenoxy, lower alkylcarbonyl, lower alkoxycarbonyl, lower alkylcarbonylamino, benzamido, 4-methylbenzoyl, phenylcarbamoyl, sulfamoyl, dilower alkylsulfamoyl, N-lower alkyl-N-phenylsulfamoyl, phenylsulfamoyl, phenylazo or 2,4-dinitroanilino, $R_{12}$ is lower alkyl, phenyl or benzyl, X is —Alk—, —Alk—Z—Alk—, —Z—Alk— or —Alk'—Z—, wherein each Alk is independently straight or branched chain lower alkylene and Z is —O—, —NH—,

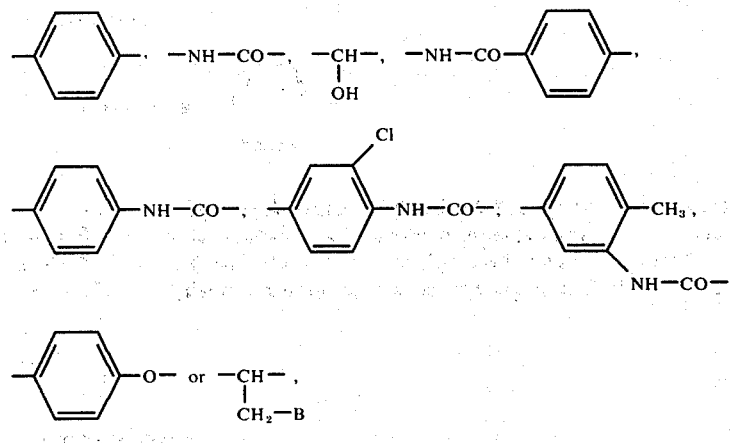

wherein

B is N,N-diloweralkylamino or piperidino, and

F' is amino, monosubstituted amino, disubstituted amino, morpholino, piperidino, piperazino, N'-lower alkylpiperazino, N'-lower alkylsulfonylpiperazino, 2-

(N-lower alkylpyrrolidyl), amidino, 2-pyridyl, 4-pyridyl or 3-(4-lower alkylpyridyl), wherein each substituent of monosubstituted amino and disubstituted amino is independently lower alkyl, lower hydroxyalkyl, lower dihydroxyalkyl, lower cyanoalkyl or lower chloroalkyl, and particularly those compounds of Formula VII wherein D' is phenyl, substituted phenyl, thiazolyl, 1,2,4-triazolonyl, methyl-1,2,4-triazolyl, indazolyl, methylindazolyl, 1,3,4-thiadiazolyl, methyl-1,3,4-thiadiazolyl or methylsulfonylbenzothiazolyl, wherein each substituent of substituted phenyl in independently methyl, methoxy, ethoxy, chloro, bromo, nitro, cyano, phenyl, phenoxy, 4-chlorophenoxy, acetyl, propionyl, methoxycarbonyl, ethoxycarbonyl, 4-methylbenzoyl, phenylcarbamoyl, sulfamoyl, dimethylsulfamoyl, n-ethyl-N-phenylsulfamoyl, phenylsulfamoyl, acetamido, benzamido, phenylazo or 2,4-dinitroanilino, $R_{12}$ is methyl, ethyl, phenyl or benzyl, X is —CH$_2$CH$_2$—, —CH$_2$CH$_2$CH$_2$—,

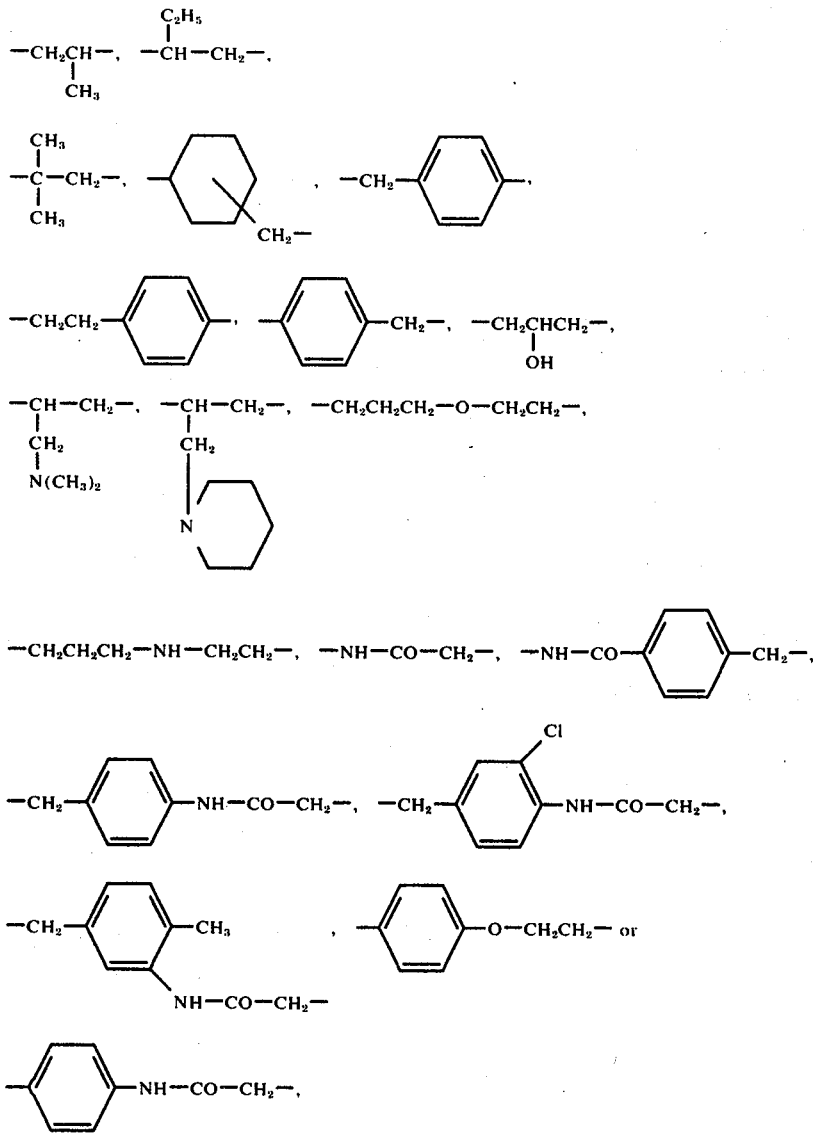

and

F' is —NH$_2$, —NHCH$_3$, —NHC$_2$H$_5$, —NH—n—C$_3$H$_7$, —NH—n—C$_4$H$_9$, —NH—C$_2$H$_4$—OH, —NH—C$_2$H$_4$—CN,

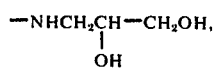

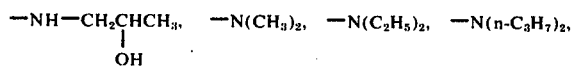

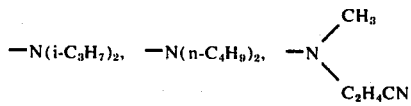

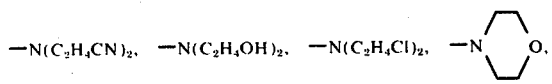

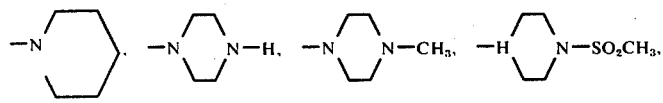

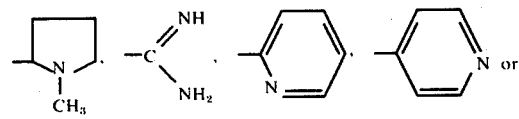

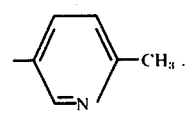

The compounds of this group wherein D' is phenyl or substituted phenyl having 1 to 3 substituents and particularly those wherein D' is phenyl, 2-methylphenyl, 3-methylphenyl, 4-methylphenyl, 2,5-dimethylphenyl, 2-methoxyphenyl, 4-methoxyphenyl, 4-ethoxyphenyl, 2-chlorophenyl, 3-chlorophenyl, 4-chlorophenyl, 2,5-dichlorophenyl, 3,4-dichlorophenyl, 2,4,5-trichlorophenyl, 2,4,6-trichlorophenyl, 2-bromophenyl, 3-bromophenyl, 2,4,6-tribromophenyl, 3chloro-4-methoxyphenyl, 2-methyl-4-chlorophenyl, 3-nitrophenyl, 4-nitrophenyl, 2,4-dinitrophenyl, 2-nitro-4-methylphenyl, 2-methyl-5-nitrophenyl, 2-nitro-4-chlorophenyl, 3-nitro-4-chlorophenyl, 2-chloro-4-nitrophenyl, 2,6-dichloro-4-nitrophenyl, 2-methoxy-4-nitrophenyl, 2-methoxy-5-nitrophenyl, 2-cyano-4-chlorophenyl, 2-phenylphenyl, 4-phenylphenyl, 3-chloro-6-phenoxyphenyl, 4-(4'-chlorophenoxy)-phenyl, 4-acetylphenyl, 4-propionylphenyl, 2-methoxycarbonylphenyl, 4-ethoxycarbonylphenyl, 4-(4'-methylbenzoyl)phenyl, 4-phenylcarbamoylphenyl, 2-methoxy-5-sulfamoylphenyl, 4-N,N-dimethylsulfamoylphenyl, 4-phenylsulfamoyl-phenyl, 2-N-ethyl-N-phenylsulfamoylphenyl, 3-phenylsulfamoyl-4-methylphenyl, 4-acetamidophenyl, 3-benzamidophenyl, 4-benzamidophenyl, 4-phenylazophenyl or 4-(2,4-dinitroanilino)phenyl are of interest.

Another group of interesting compounds are the compounds of the formula

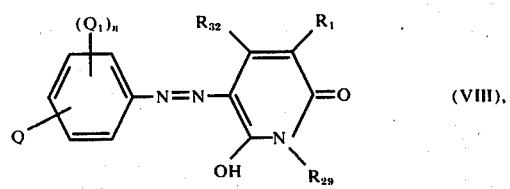

wherein
Q is —CO—NH—$C_2H_4$—N($CH_3$)$_2$, —CO—NH—$CH_2CH_2CH_2$N($CH_3$)$_2$, —CO—N($CH_3$)$C_2H_4$N($CH_3$)$_2$, —CO—$CH_2$—N($CH_3$)$_2$, —CO—$CH_2$—N($C_2H_4$OH)$_2$,

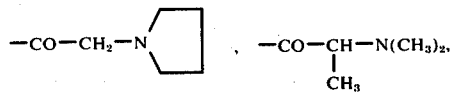

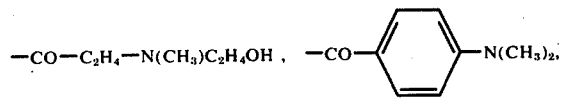

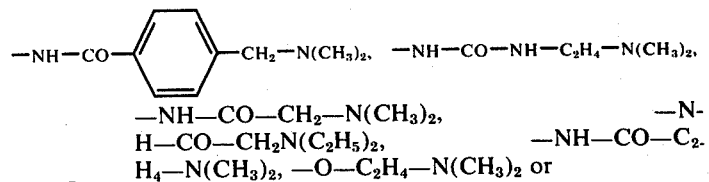

—NH—CO—$CH_2$—N($CH_3$)$_2$, —NH—CO—$CH_2$N($C_2H_5$)$_2$, —NH—CO—$C_2H_4$—N($CH_3$)$_2$, —O—$C_2H_4$—N($CH_3$)$_2$ or

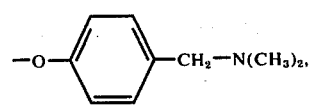

$Q_1$ is chloro, bromo, methyl, ethyl, methoxy, ethoxy or phenoxy, $R_1$ is hydrogen or cyano, $R_{29}$ is hydrogen, methyl, ethyl, cyclohexyl, phenyl, benzyl, 3-methoxypropyl, 3-N,N-dimethylaminopropyl, 2-morpholinoethyl, 2-(2-pyridyl)ethyl, 4-(2-N,N-dimethylaminoethyl)phenyl, amino or dimethylamino, $R_{32}$ is methyl or phenyl, and $n$ is 0 or 1,
and especially those wherein Q is —CO—NH—$C_2H_4$—N($CH_3$)$_2$, —CO—N($CH_3$)$C_2H_4$—N($CH_3$)$_2$, —CO—$CH_2$—N($C_2H_4OH$)$_2$, —CO—$C_2H_4$—N($CH_3$)$C_2H_4OH$,

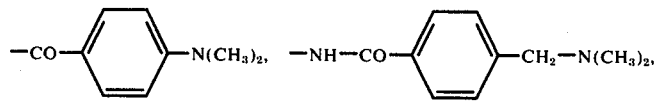

—NH—CO—NH—$C_2H_4$—N($CH_3$)$_2$, —NH—CO—$CH_2$—N($CH_3$)$_2$, —NH—CO—$C_2H_4$—N($CH_3$)$_2$, —O—$C_2H_4$—N($CH_3$)$_2$ or

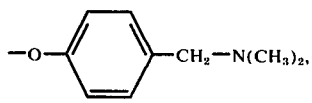

$Q_1$ is chloro, bromo, methyl, ethyl, methoxy or phenoxy,
$R_1$ is hydrogen or cyano,
$R_{29}$ is methyl, ethyl, phenyl or cyclohexyl,
$R_{32}$ is methyl, and
$n$ is 0 or 1.

The compounds of Formula I can be synthesized by diazotizing an amine of the formula D-$NH_2$ and reacting the resulting diazonium compound with a pyridone of the formula

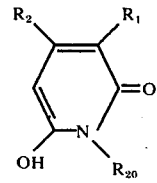

(IX)

wherein $R_1$, $R_2$ and $R_{20}$ are as defined above.
Particularly useful are pyridones of the formula

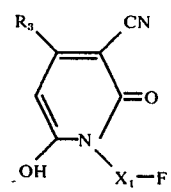

(X), wherein $R_3$ is alkyl of 1 to 12 carbon atoms, phenyl or benzyl,
$X_1$ is straight or branched chain alkylene of 1 to 12 carbon atoms,

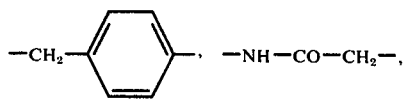

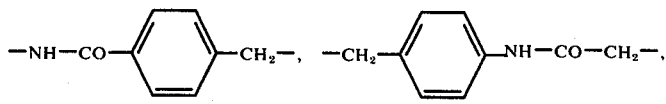

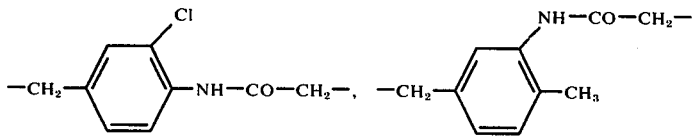

or

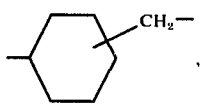

and
F is amino, lower alkylamino, dilower alkylamino, lower hydroxyalkylamino, lower dihydroxyalkylamino, lower cyanoalkylamino, N-lower alkyl-N-lower cyanoalkylamino, dilower hydroxyalkylamino, dilower cyanoalkylamino,

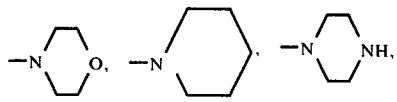

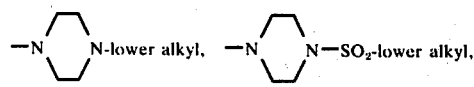 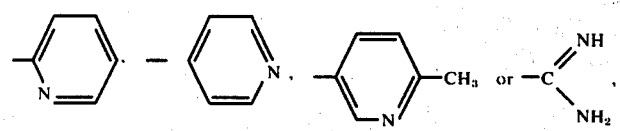

and especially those compounds wherein $R_3$ is alkyl (especially methyl) or phenyl as well as those compounds wherein $R_3$ is methyl, ethyl, phenyl or benzyl, $X_1$ is —CH$_2$CH$_2$—, —CH$_2$CH$_2$CH$_2$—,

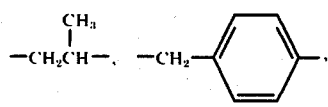

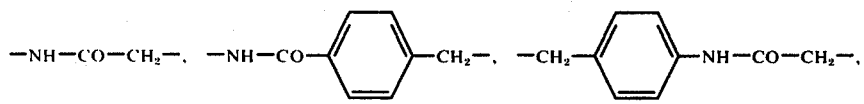

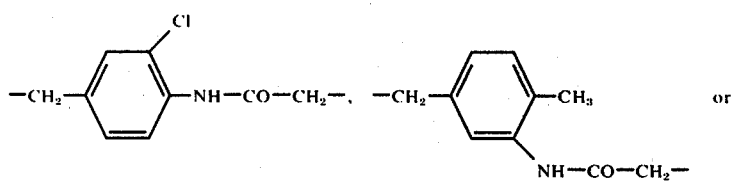

and
F is —NH$_2$, —NH—CH$_3$, —NHC$_2$H$_5$, —NHC$_2$H$_4$OH, —NH—C$_2$H$_4$CN,

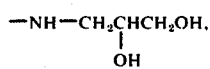

—NH—CH$_2$CH$_2$CH$_3$, —NH—CH$_2$CH$_2$CH$_2$CH$_3$, —N(CH$_3$)$_2$, N(C$_2$H$_5$)$_2$, —N(CH$_2$CH$_2$CH$_2$CH$_3$)$_2$, —N(CH$_3$)C$_2$H$_4$CN, —N(C$_2$H$_4$CN)$_2$, —N(C$_2$H$_4$OH)$_2$, $X_1$ is —CH$_2$CH$_2$— or —CH$_2$CH$_2$CH$_2$— and
F is —NH$_2$, —NHCH$_3$, —NHC$_2$H$_5$, —NH—CH$_2$CH$_2$CH$_3$, —NHCH$_2$CH$_2$CH$_2$CH$_3$, —N(CH$_3$)$_2$, —N(C$_2$H$_5$)$_2$ or —N(CH$_2$CH$_2$CH$_2$CH$_3$)$_2$.

Compounds of the formula

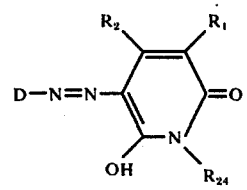

wherein $R_{24}$ is

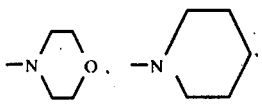

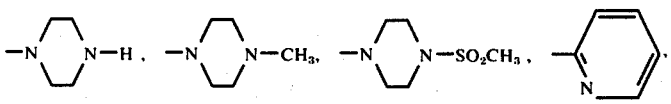

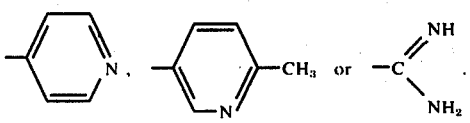

Especially preferred are the compounds of this group wherein

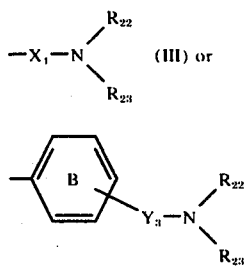 (III) or wherein $Y_3$ is alkylene which may be interrupted by hetero atoms and may be substituted, can be synthesized by reacting a compound of the formula

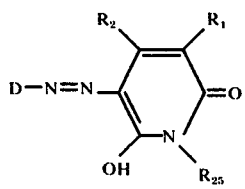 (XII), wherein $R_{25}$ is

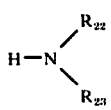 or wherein A is the acid radical of an ester, with an amine of the formula

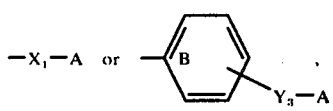 (XIII).

The preferred A radicals are those of the hydrohalide acids. A is preferably chloro or bromo. A can also be a radical of sulfuric acid, a sulfonic acid or hydrogen sulfide.

The coupling of a diazotized amine of the formula $D-NH_2$ with a pyridone coupling component can be carried out by known methods. The reaction of a compound of Formula XIII with a compound of Formula XII is preferably carried out in an organic solvent at a temperature of $-50°$ C. to $+250°$ C., preferably at $-10°$ C. to $+120°$ C. The reaction can alternatively be carried out in an aqueous medium with the addition of an organic solvent or in the absence of solvent at the aforestated temperatures.

The coupling components, e.g., of Formula IX, can be prepared by the methods described by J. Guareschi, Atti Accad. R. d. Scienze di Torino, 1895/96; Chem. Ber. 29, 655 (1896);Chem. Zentr. 1896, I, 602; 1896, II, 46; and Umaprasynna Basu, J. Indian Chem. Soc. 8, 319–328 (1931) by condensation of substituted or unsubstituted acetic acid amides or hydrazides with correspondingly substituted β-ketocarboxylic acid esters.

It is desirable to convert the resulting dyes into stabilized, solid dye preparations or stable, concentrated, aqueous dye solutions.

The new dyes are employed for the dyeing and printing of textiles which consist of or which contain polyacrylonitrile or acrylonitrile copolymer fibers. They are also employed for the exhaust dyeing, pad dyeing and printing of polyamide fibers and polyester fibers modified by the introduction of acid groups. Polyamide fibers of this type are disclosed, for example, in Belgian Pat. No. 706,104. The analogous polyesters are disclosed in U.S. Pat. Nos. 3,018,272 and 3,379,723. It is normally advantageous to dye from an cationic neutral or acid medium at a temperature of $60°-100°$ C. or at a temperature above $100°$ C. under static pressure. Level dyeings are obtained without the assistance of retarders. Blend fabrics containing a component of acrylic fiber can be successfully dyed with these dyes. The dyes of the present invention which have good solubility in organic solvents are also suitable for the mass pigmentation of natural and synthetic resins and plastics. It has been found that mixtures of two or more of the new dyes or mixtures of these and ccationic dyes can be successfully applied, i.e., the dyes are well suitable for combined application. They can also be employed for dyeing paper and leather.

Level dyeings of good light and wet fastness are obtained on polyacrylonitrile and acrylonitrile copolymer fibers as well as on the aforenamed substrates. The high tinctorial strength of the new dyes is a noteworthy feature.

The dye of the formula

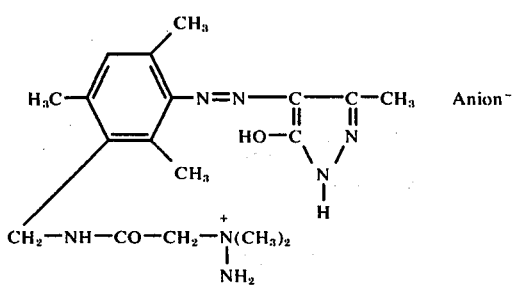

disclosed in Belgian Pat. No. 633,447 is employed, among other purposes, for dyeing polyacrylonitrile fibers. In comparison with it the dyes of Formula I build up more powerfully on polyacrylonitrile fibers, giving dyeings of greater depth and of superior light fastness.

Dyeings produced with dyes of Formula I have good fastness to washing, perspiration, sublimation, pleating, decatizing, pressing, steaming, water, sea water, dry cleaning, cross dyeing and solvents. They show good compatibility with salts, are well soluble, especially in water, have good stability to pH conditions and boiling, and reserve natural and synthetic polyamide fibers.

It is assumed that the compounds bearing a dihydroxypyridone radical are present in a tautomeric state, as exemplified by the following formulae:

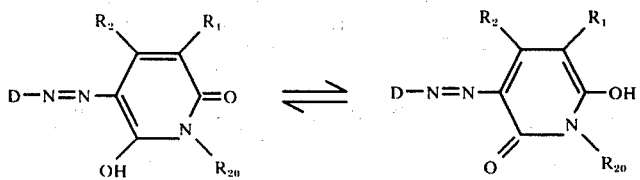

In the following Examples the parts and percentages are by weight and the temperatures in degrees centigrade.

EXAMPLE 1

17.8 Parts of 4-amino-ω-dimethylamino-acetophenone (prepared by reacting 4-acetamino-ω-chloracetophenone with dimethylamine and saponifying the acetamino group with hydrochloric acid) are diazotized at 0° by the normal method. The pH is adjusted to 8.0 with sodium carbonate and over one hour a solution of 17 parts of 2,6-dihydroxy-4-methyl-5-cyanopyridine in 200 parts of water, likewise of pH 8.0, is dropped in. On completion of coupling the separated dye is filtered off, washed with water, dried and ground. The new dye, e.g., as hydrochloride, is well soluble in water and is suitable for dyeing polyacrylonitrile fibres in fast greenish yellow shades. In place of dimethylamine the equivalent amount of pyrrolidine can be employed using the same procedure as above, whereupon a similar dye is obtained.

DYEING METHOD

One part of the dye of Example 1 and one part of 40% acetic acid are pasted, 400 parts of distilled water at 60° are run over the paste with constant stirring and with boiling for a short time to complete dissolving. The solution is added to 7600 parts of distilled water, with the subsequent addition of 2 parts of glacial acetic acid. 100 Parts of a fabric of polyacrylonitrile fibre are entered into this dyebath at 60°, after previous treatment for 10–15 minutes at 60° in a bath of 8000 parts of water and 2 parts of glacial acetic acid. The dyebath is raised to 100° over 30 minutes and held at the boil for 1 hour. On removal the fabric is washed off. A level greenish yellow dyeing is obtained which has excellent light and very good wet fastness properties. Similar dyeings showing the same good fastness properties as the dye of Example 1 are obtained when the 17 parts of 2,6-dihydroxy-4-methyl-5-cyanopyridine are replaced by the equivalent amount of 1-(3'-dimethylamino)-propyl-2-keto-3-cyano-4-methyl-6-hydroxy-1,2-dihydropyridine, 1-benzyl-2-keto-3-cyano-4-methyl-6-hydroxy-1,2-dihydropyridine, 1-methyl-2-keto-3-cyano-4-phenyl-6-hydroxy-1,2-dihydropyridine, 1-(2'-morpholinylethyl)-2-keto-3-cyano-4-methyl-6-hydroxy-1,2-dihydropyridine, 1-[4'-ω''-dimethylamino-ethoxy]-phenyl-2-keto-3-cyano-4-methyl-6-hydroxy-1,2-dihydropyridine, 1-(3'-methoxypropyl)-2-keto-3-cyano-6-hydroxy-1,2-dihydropyridine, 1-[2'-pyridinyl-(2)]-ethyl-2-keto-3-cyano-4-methyl-6-hydroxy-1,2-dihydropyridine, 1-dimethylamino-2-keto-3-cyano-4-methyl-6-hydroxy-1,2-dihydropyridine or 1-amino-2-keto-3-cyano-4-methyl-6-hydroxy-1,2-dihydropyridine.

EXAMPLE 2

13.7 Parts of nitrosylsulfuric acid are added at 0° over one hour to a solution of 10 parts of 2-aminothiazole in 100 parts of sulphuric acid of 16° Tw. The resulting diazo solution is run onto 150 parts of ice and the excess acid decomposed with aminosulphonic acid. In the course of one hour a solution of 25.9 parts of 1-(3'-dimethylamino)-propyl-4-keto-3-cyano-4-methyl-6-hydroxy-1,2-dihydroxypyridine in 50 parts of water is added dropwise to the diazo solution, followed by 60 parts of common salt. The dye is isolated in the normal manner. On drying and grinding it is obtained as a water soluble powder which is highly suitable for dyeing polyacrylonitrile fibres in fast, neutral yellow shades. Similar dyes showing equally good fastness properties are obtained when the 25.9 parts of 1-(3'-dimethylamino)-propyl-2-keto-3-cyano-4-methyl-6-hydroxy-1,2-dihydropyridine used in Example 2 are replaced by the equivalent amount of 1-(3'-dimethylamino)-propyl-2-keto-3-cyano-4-phenyl-6-hydroxy-1,2-dihydropyridine, 1-[4'-(ω''-dimethylamino)-acetamino]-phenyl-2-keto-3-cyano-4-methyl-6-hydroxy-1,2-dihydropyridine, 1-[2'-pyridinyl-(2)]-ethyl-2-keto-3-cyano-4-methyl-6-hydroxy-1,2-dihydropyridine, 1-[2'-pyridinyl-(4)]-ethyl-2-keto-3-cyano-4-phenyl-6-hydroxy-1,2-dihydropyridine, 1-dimethylamino-2-keto-3-cyano-4-methyl-6-hydroxy-1,2-dihydropyridine or 1-amino-2-keto-3-cyano-4-methyl-6-hydroxy-1,2-dihydropyridine, or by replacing the diazo component by an equivalent amount of 2-amino-1,2,4-triazolone, 3-methyl-5-amino-1,2,4-triazole, 3-aminoindazole, 4-methyl-3-aminoindazole, 2-amino-1,3,4-thiadiazole, 2-amino-4-methyl-1,3,4-thiadiazole, 2-amino-4-methyl-1,3,4-thiadiazole, ω-dimethylamino-4-aminoacetophenone, 2'-dimethylamino-4-aminopropiophenone, 1-(ω-dimethylamino)-acetamino-4-aminobenzene or 1-(ω-diethylamino)-acetamino-4-aminobenzene, 1-amino-4-nitro-2-chlorobenzene, 1-amino-2-nitro-4-methylbenzene, 1-aminobenzene-4-sulphodimethylamide, 1-amino-4-acetylbenzene, 4-aminobenzoic acid ethylester, 1-amino-2,5-dichlorobenzene or 1-amino-2,4-dinitrobenzene.

EXAMPLE 3

Diazotization of 12.32 parts of 1-amino-2-methoxybenzene is carried out by the known method and to the ice-cold mineral acid diazo solution is added with stirring a solution of 25 parts of 1-(3'-dimethylaminopropyl)-2-keto-3-cyano-4-methyl-6-hydroxy-1,2-dihydropyridine in 80 parts of water. Stirring is continued at 0°. The dye formed is salted out at 80° with sodium chloride, filtered off and dried. Applied from aqueous medium, it gives dyeings of bright reddish yellow shade on polyacrylonitrile fibres which show high light and wet fastness.

In place of the 25 parts of 1-(3'-dimethylaminopropyl)-2-keto-3-cyano-4-methyl-6-hydroxy-1,2-dihydropyridine an equivalent amount of a compound of the formula

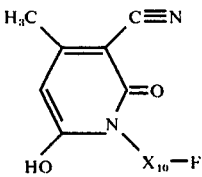

can be employed, the operating procedure being otherwise as given in this Example.

These dyes have similarly good properties, in which $X_{10}$ stands for one of the following radicals:

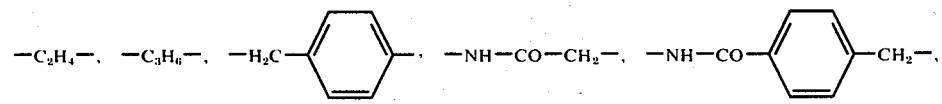

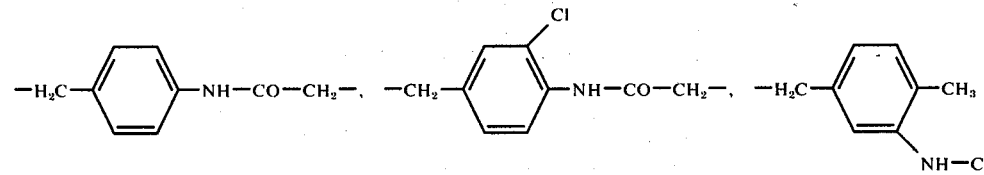

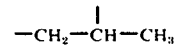

and F stands for one of the radicals listed in Table A on page 30. In any given dye these groupings can be exchanged for any other of the stated groupings.

EXAMPLE 4

23.3. Parts of 4-amino-3-methylbenzoic acid-3'-dimethylamino-n-propylamide are diazotized in the normal way and the hydrochloric acid diazo solution is entered into an ice-cold aqueous suspension of 26.2 parts of 1-methyl-2-keto-3-cyano-4-methyl-6-hydroxy-1,2-dihydropyridine. The pH of the reaction mixture is adjusted to 3.0 by dropping in 50% aqueous acetate solution. Subsequently the dye is salted out with common salt, collected on a filter and dried. It is water soluble and gives fast greenish yellow dyeings on polyacrylonitrile fibres.

Dyes of the same high quality are obtained when the 23.3 parts of 4-amino-3-methyl-benzoic acid-3'-dimethylamino-n-propylamide used in this Example are replaced by the equivalent amount of the diazo compound of an amine of the formula

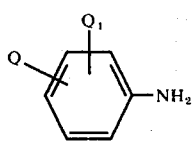

where Q represents a radical of the formula $-CO-NH-C_2H_4-N(CH_3)_2,$

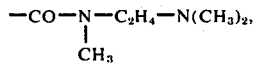

$-CO-CH_2-N(C_2H_4OH)_2,$

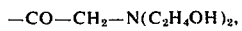

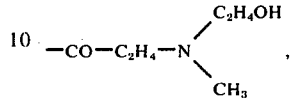

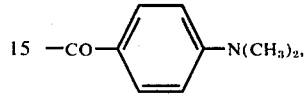

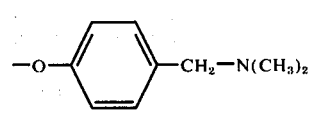

$-NH-CO-NH-C_2H_4-N(CH_3)_2,$ $-NH-CO-CH_2-N(CH_3)_2,$ $-NH-CO-C_2H_4-N(CH_3)_2,$ $-O-C_2H_4-N(CH_3)_2$ or

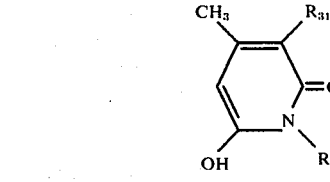

and $Q_1$ represents hydrogen, chlorine, bromine, methyl, ethyl, methoxy ethoxy or phenoxy, with a coupling component of the formula

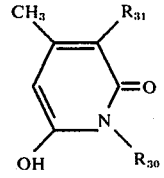

(d)

where $R_{30}$ represents methyl, ethyl, phenyl or cyclohexyl and $R_{31}$ stands for hydrogen or —CN. The coupling components wherein $R_{31}$ stands for hydrogen may be obtained by splitting off the —CN group from compounds of formula (d) in strong acid medium.

EXAMPLE 5

At 0°–5° 30 parts of 23% sodium nitrite solution was run into a suspension of 17.23 parts of 1-amino-3-nitro-4-chlorobenzeno in 200 parts of 6% hydrochloric acid. The resulting diazo solution is diluted with 200 parts of ice-water and to it is added an aqueous hydrochloric acid solution of 24 parts of 1-(3'-N',N'-dimethylaminopropyl)-2-keto-3-cyano-4-methyl-6-hydroxy-1,2-dihydropyridine. After coupling, the dye formed is precipitated with sodium chloride in the form of the hydrochloride, collected on a filter and dried. It can be purified by recrystallization, e.g., from acetic acid. It is ground to a yellow powder which dissolves in water and dyes polyacrylonitrile fibres in bright yellow shades of good light and wet fastness.

For the preparation of 1-(3'-N',N'-dimethylaminopropyl)-2-keto-3-cyano-4-methyl-6-hydroxy-1,2-dihydropyridine, cyanoacetic ester is reacted with 3-dimethylaminopropylamine by the known method to give cyanoacetic acid-3-dimethylaminopropylamide and this is condensed in the known way to 1-(3'-N',N'-dimethylaminopropyl)-2-keto-3-cyano-4-methyl-6-hydroxy-1,2-dihydropyridine.

DYEING EXAMPLE

A mixture of 20 parts of the dye of Example 5 and 80 parts of dextrin is ground in a ball mill for 48 hours. One part of the resulting preparation and one part of 40% acetic acid are pasted and dissolved in 200 parts of demineralized water with boiling, the solution is added to 7000 parts of softened water and the bath set with 2 parts of glacial acetic acid. 100 Parts of a polyacrylonitrile fabric are entered into the bath at 60°. The material may be pretreated for 10–15 minutes at 60° in a bath of 8000 parts of water and 2 parts of glacial acetic acid. The dyebath is raised to 98°–100° over 30 minutes and held at the boil for 1 ½ hours. A yellow dyeing of good light and wet fastness is obtained.

The following table gives the structures of other dyes which can be produced in accordance with the procedure of Example 5, i.e., by diazotizing an amine of the formula D'-NH₂ and coupling the resulting diazonium compound with a pyridone of the formula

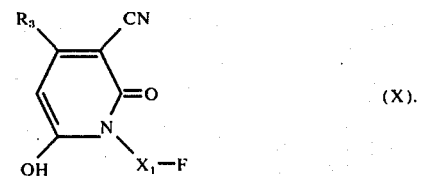

(X).

Thus, for example, the dyes of Examples 6–10, 12, 33, 35, 56, 58 and 79 are synthesized by diazotizing the amine of the D'—NH₂ column and coupling the resulting diazonium compound with the coupling component of the pyridone column.

-continued

| Ex. No. | D'—NH$_2$ | Pyridone |
|---|---|---|
| 9 | 6-(methylsulfonyl)benzothiazol-2-amine (CH$_3$SO$_2$ substituted benzothiazole-2-NH$_2$) | 3-cyano-6-hydroxy-4-methyl-1-[2-(dimethylamino)ethyl]pyridin-2(1H)-one |
| 10 | 4-chloro-2-nitroaniline | 1-(2-aminoethyl)-3-cyano-6-hydroxy-4-methylpyridin-2(1H)-one |
| 12 | " | 3-cyano-1-[2-(ethylamino)ethyl]-6-hydroxy-4-methylpyridin-2(1H)-one |
| 33 | " | 1-(3-aminopropyl)-3-cyano-6-hydroxy-4-methylpyridin-2(1H)-one |
| 35 | " | 3-cyano-1-[3-(ethylamino)propyl]-6-hydroxy-4-methylpyridin-2(1H)-one |
| 56 | " | 1-(2-aminoethyl)-3-cyano-6-hydroxy-4-phenylpyridin-2(1H)-one |
| 58 | " | 3-cyano-1-[2-(ethylamino)ethyl]-6-hydroxy-4-phenylpyridin-2(1H)-one |

-continued

| Ex. No. | D'—NH$_2$ | Pyridone |
|---------|-----------|----------|
| 79 | " | 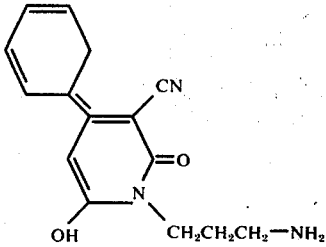 |

The pyridone of Example 10 is N-β-aminoethyl-3-cyano-4-methyl-6-hydroxy-2-pyridone.

The dyes produced have the formula

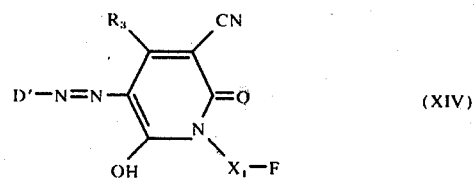     (XIV)

wherein D', $R_3$, $X_1$ and F have one of the meanings stated in the table. The symbol F may stand for any one of the radicals F listed in Table A. In any given dye these groupings may be replaced by any other of the stated groupings.

Table A

F may stand for any one of the symbols $F_1$ to $F_{23}$ which represent the groupings listed below.

Table A

| | | |
|---|---|---|
| $F_1$ | represents | —NH$_2$ |
| $F_2$ | " | —NH—CH$_3$ |
| $F_3$ | " | —NH—C$_2$H$_5$ |
| $F_4$ | " | —NH—C$_2$H$_4$—OH |
| $F_5$ | " | —NH—C$_2$H$_4$—CN |
| $F_6$ | " | —NH—CH$_2$—CHOH—CH$_2$—OH |
| $F_7$ | " | —NH—C$_3$H$_7$(n) |
| $F_8$ | " | —NH—C$_4$H$_9$(n) |
| $F_9$ | " | —N(CH$_3$)$_2$ |
| $F_{10}$ | " | —N(C$_2$H$_5$)$_2$ |
| $F_{11}$ | " | —N(C$_4$H$_9$)$_2$(n) |
| $F_{12}$ | " | 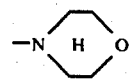 |
| $F_{13}$ | " | 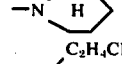 |
| $F_{14}$ | " | 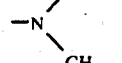 |
| $F_{15}$ | " | —N(C$_2$H$_4$CN)$_2$ |
| $F_{16}$ | " | —N(C$_2$H$_4$OH)$_2$ |
| $F_{17}$ | " | 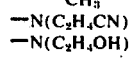 |
| $F_{18}$ | " | 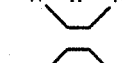 |
| $F_{19}$ | " | 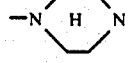 |
| $F_{20}$ | " | 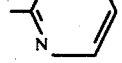 |
| $F_{21}$ | " | 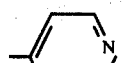 |

Table A-continued

| | F22 | " | C(=NH)NH2 | | |
| | F23 | " | -N(piperazine-H)N-CH3 | | |

| Ex. No | D' | X1 | F | R3 | Shade of dyeing on polyacrylonitrile |
|---|---|---|---|---|---|
| 6 | 3-NO2-C6H4- | —C2H4— | F1 | —CH2—C6H5 | yellow |
| 7 | " | " | F9 | —C2H5 | " |
| 8 | " | —C3H6— | F9 | " | " |
| 9 | 6-Methylsulphonyl-benzothiazolyl-2 | " | F9 | —CH3 | " |
| 10 | 5-Cl-2-CH3-3-NO2-C6H2- | —C2H4— | F1 | —CH3 | " |
| 11 | " | " | F2 | " | " |
| 12 | " | " | F3 | " | " |
| 13 | " | " | F4 | " | " |
| 14 | " | " | F5 | " | " |
| 15 | " | " | F6 | " | " |
| 16 | " | " | F7 | " | " |
| 17 | " | " | F8 | " | " |
| 18 | " | " | F9 | " | " |
| 19 | " | " | F10 | " | " |
| 20 | " | " | F11 | " | " |
| 21 | " | " | F12 | " | " |
| 22 | " | " | F13 | " | " |
| 23 | " | " | F14 | " | " |
| 24 | " | " | F15 | " | " |
| 25 | " | " | F16 | " | " |
| 26 | " | " | F17 | " | " |
| 27 | " | " | F18 | " | " |
| 28 | " | " | F19 | " | " |
| 29 | " | " | F20 | " | " |
| 30 | " | " | F21 | " | " |
| 31 | " | " | F22 | " | " |
| 32 | " | " | F23 | " | " |
| 33 | " | —CH2—CH2—CH2— | F1 | " | " |
| 34 | " | " | F2 | " | " |
| 35 | " | " | F3 | " | " |
| 36 | " | " | F4 | " | " |
| 37 | " | " | F5 | " | " |
| 38 | " | " | F6 | " | " |
| 39 | " | " | F7 | " | " |
| 40 | " | " | F8 | " | " |
| 41 | " | " | F9 | " | " |
| 42 | " | " | F10 | " | " |
| 43 | " | " | F11 | " | " |
| 44 | " | " | F12 | " | " |
| 45 | " | " | F13 | " | " |
| 46 | " | " | F14 | " | " |
| 47 | " | " | F15 | " | " |
| 48 | " | " | F16 | " | " |
| 49 | " | " | F17 | " | " |
| 50 | " | " | F18 | " | " |
| 51 | " | " | F19 | " | " |
| 52 | " | " | F20 | " | " |
| 53 | " | " | F21 | " | " |
| 54 | " | " | F22 | " | " |
| 55 | " | " | F23 | " | " |
| 56 | " | —C2H4— | F1 | —C6H5 | " |
| 57 | " | " | F2 | " | " |
| 58 | " | " | F3 | " | " |
| 59 | " | " | F4 | " | " |
| 60 | " | " | F5 | " | " |
| 61 | " | " | F6 | " | " |
| 62 | " | " | F7 | " | " |
| 63 | " | " | F8 | " | " |
| 64 | " | " | F9 | " | " |
| 65 | " | " | F10 | " | " |
| 66 | " | " | F11 | " | " |
| 67 | " | " | F12 | " | " |
| 68 | " | " | F13 | " | " |
| 69 | " | " | F14 | " | " |
| 70 | " | " | F15 | " | " |
| 71 | " | " | F16 | " | " |
| 72 | " | " | F17 | " | " |

Table A-continued

| No. | | R (middle col) | F (dye) | | |
|---|---|---|---|---|---|
| 73 | " | " | $F_{18}$ | " | " |
| 74 | " | " | $F_{19}$ | " | " |
| 75 | " | " | $F_{20}$ | " | " |
| 76 | " | " | $F_{21}$ | " | " |
| 77 | " | " | $F_{22}$ | " | " |
| 78 | " | " | $F_{23}$ | " | " |
| 79 | " | $-CH_2-CH_2-CH_2-$ | $F_1$ | " | " |
| 80 | " | " | $F_2$ | " | " |
| 81 | " | " | $F_3$ | " | " |
| 82 | " | " | $F_4$ | " | " |
| 83 | " | " | $F_5$ | " | " |
| 84 | " | " | $F_6$ | " | " |
| 85 | " | " | $F_7$ | " | " |
| 86 | " | " | $F_8$ | " | " |
| 87 | " | " | $F_9$ | " | " |
| 88 | " | " | $F_{10}$ | " | " |
| 89 | " | " | $F_{11}$ | " | " |
| 90 | " | " | $F_{12}$ | " | " |
| 91 | " | " | $F_{13}$ | " | " |
| 92 | " | " | $F_{14}$ | " | " |
| 93 | " | " | $F_{15}$ | " | " |
| 94 | " | " | $F_{16}$ | " | " |
| 95 | " | " | $F_{17}$ | " | " |
| 96 | " | " | $F_{18}$ | " | " |
| 97 | " | " | $F_{19}$ | " | " |
| 98 | " | " | $F_{20}$ | " | " |
| 99 | " | " | $F_{21}$ | " | " |
| 100 | " | " | $F_{22}$ | " | " |
| 101 | " | " | $F_{23}$ | " | " |
| 102 | " | " | $F_4$ | $-CH_3$ | " |
| 103 | " | $-H_2C-\langle\phantom{x}\rangle-$ | $F_9$ | " | " |
| 104 | " | " | $F_{17}$ | " | " |
| 105 | " | $-NH-CO-CH_2-$ | $F_4$ | " | " |
| 106 | " | " | $F_9$ | " | " |
| 107 | " | " | $F_{17}$ | " | " |
| 108 | " | $-NH-CO-\langle\phantom{x}\rangle-CH_2-$ | $F_4$ | " | " |
| 109 | " | " | $F_9$ | " | " |
| 110 | " | " | $F_{17}$ | " | " |
| 111 | " | $-H_2C-\langle\phantom{x}\rangle-NH-CO-CH_2-$ | $F_4$ | " | " |
| 112 | " | " | $F_9$ | " | " |
| 113 | " | " | $F_{17}$ | " | " |
| 114 | " | $-H_2C-\langle\text{Cl}\rangle-NH-CO-CH_2-$ | $F_4$ | " | " |
| 115 | " | " | $F_9$ | " | " |
| 116 | " | " | $F_{17}$ | " | " |
| 117 | " | " | | " | " |
| 118 | " | $-H_2C-\langle\text{CH}_3\rangle-NH-CO-CH_2-$ | $F_4$ | " | " |
| 119 | " | " | $F_9$ | " | " |
| 120 | " | " | $F_{17}$ | " | " |
| 121 | " | $-CH_2-CH(CH_3)-CH_3$ | $F_4$ | $\langle\phantom{x}\rangle$ | |
| 122 | " | " | $F_9$ | " | " |
| 123 | " | " | $F_{17}$ | " | " |
| 124 | " | $-NH-CO-CH_2-$ | $F_4$ | " | " |
| 125 | " | " | $F_9$ | " | " |
| 126 | " | " | $F_{17}$ | " | " |
| 127 | " | $-NH-CO-\langle\phantom{x}\rangle-CH_2-$ | $F_4$ | " | " |
| 128 | " | " | $F_9$ | " | " |
| 129 | " | " | $F_{17}$ | " | " |
| 130 | " | $-H_2C-\langle\phantom{x}\rangle-$ | $F_4$ | " | " |
| 131 | " | " | $F_9$ | " | " |
| 132 | " | " | $F_{17}$ | " | " |

The 17.25 parts of 1-amino-3-nitro-4-chlorobenzene used in Example 5 can be replaced by the equivalent amount of one of the amines named below, whereupon dyes having equally good properties are obtained. These dyes give dyeings of yellow to reddish yellow shade on polyacrylonitrile fibres.

1-amino-2-nitro-4-methylbenzene
1-amino-4-benzoylaminobenzene
1-amino-4'-chlorodiphenylether
1-amino-4-N,N-dimethylsulfamoylbenzene
1-amino-2-chlorobenzene
1-amino-4-chlorobenzene 1-amino-3-chlorobenzene
1-amino-2,5-dichlorobenzene
1-amino-3,4-dichlorobenzene
1-amino-2-bromobenzene
1-amino-3-bromobenzene
1-amino-2,4,6-tribromobenzene
1-amino-2,4,6-trichlorobenzene
1-amino-2-methoxybenzene
1-amino-2-methylbenzene
1-amino-3-methylbenzene
1-amino-4-methylbenzene
1-amino-2,5-dimethylbenzene
1-amino-2-methoxybenzene-5-sulphonamide
1-amino-4-nitrobenzene
1-amino-3-nitrobenzene
aminobenzene
1-amino-2-methoxy-4-nitrobenzene
1-amino-2-methoxy-5-nitrobenzene
1-amino-3-chloro-4-methoxybenzene
1-amino-4-acetylaminobenzene
1-amino-4-methoxybenzene
1-amino-4-ethoxybenzene
1-amino-2,6-dichloro-4-nitrobenzene
1-amino-2,4,5-trichlorobenzene
4-amino-4-chlorodiphenylether.

EXAMPLE 133

9.3 Parts of aminobenzene are diazotized in 300 parts of 4% hydrochloric acid by the normal method. Subsequently a solution of 29 parts of 1-(4'-dimethylaminomethylphenyl)-2-keto-3-cyano-4-methyl-6-hydroxy-1,2-dihydropyridine (prepared by reacting cyanoacetic acid ethylester with 4-amino-N',N'-dimethylbenzylamine to 4-cyanoacetamido-N',N'-dimethylbenzylamine and condensing this with acetoacetic acid ethylester in the presence of morpholine) in 50 parts of glacial acetic acid is added dropwise at 0°. At the same time 100 parts of a 12.5% aqueous sodium acetate solution are added. On completion of the coupling reaction the mixture is raised to 60° and rendered acidic with hydrochloric acid. The dye, which is present as the hydrochloride, is salted out and isolated by filtration. It can be purified by recrystallization. On drying and grinding it is obtained as a water soluble powder which gives yellow dyeings of excellent fastness on polyacrylonitrile fibres.

EXAMPLE 134

17 Parts of 1-amino-2-nitro-4-methylbenzene are diazotized by the normal method and coupled with 25 parts of a compound of the formula

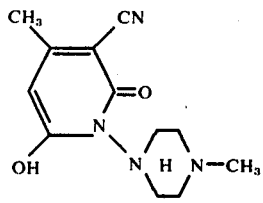

(a), in aqueous hydrochloric acid solution. After coupling, the dye formed is precipitated with sodium chloride in the form of the hydrochloride. It is ground to give a yellow powder which as a hydrochloride dissolves in water. It gives dyeings of bright yellow shade with high and wet fastness on polyacrylonitrile fibres.

The aforestated coupling component of formula (a) can be replaced by the equivalent amount of the coupling component of the formula

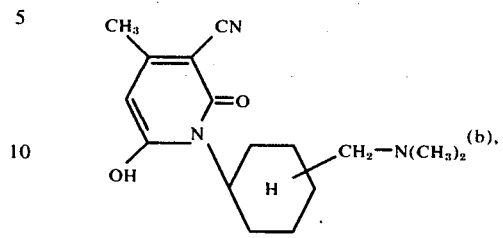

(b), on which a yellow dye with the same good properties is obtained.

EXAMPLE 135

10.7 Parts of 1-amino-4-methylbenzene are diazotized with 6.9 parts of sodium nitrite in 200 parts of 6% hydrochloric acid at 0°. To the ice-cold azo solution is added over one hour a solution of 23 parts of 1-[pyridyl-(2)]-2-keto-3-cyano-4-methyl-6-hydroxy-1,2-dihydropyridine, 30 parts of dimethylformamide and 70 parts of methanol. The reaction mixture is adjusted to pH 4.0 with sodium acetate and stirred until the coupling reaction has run its course. The dye settles out and is filtered off, washed with water and dried. It is obtained as a water soluble yellow powder which gives very fast yellow dyeings on polyacrylonitrile fibres.

A similar, equally valuable dye is obtained when the 10.7 parts of 1-amino-4-methylbenzene used are replaced by 13.5 parts of 1-amino-4-acetylbenzene and the procedure of this Example is followed in all other respects.

The coupling component used is prepared by condensation of the reaction product of cyanoacetic acid ethylester and 2-aminopyridine with acetoacetic acid ethylester in the presence of a secondary amine, e.g., morpholine.

EXAMPLE 136

19.7 Parts of 4-amino-1,1'-azobenzene, after diazotization in the known way with 6.9 parts of sodium nitrite in 200 parts of 6% hydrochloric acid, are entered into a solution of 21.5 parts of 1-(2'-hydroxyethyl)-2-keto-3-cyano-4-methyl-6-hydroxy-1,2-dihydroxypyridine and 120 parts of methyl alcohol. The reaction mixture is adjusted to pH 4.0 with sodium carbonate and stirred further until the coupling reaction is complete. 20.1 Parts of the dye so formed are dissolved in 180 parts of dimethylformamide. At room temperature 5.6 parts of thionyl chloride are added to the solution, which is then stirred for 45 minutes at 60°. The chlorinated dye is precipitated by dilution with water, collected on a filter, washed with water and dried. 21 Parts of this dye are added to 200 parts of dimethylformamide and 7.1 parts of dimethylamine and the solution is maintained at 70° for one hour. The dye solution is then rendered acidic with hydrochloric acid and sodium chloride is added thereto, causing the dye to settle out as the hydrochloride. It is in the form of an orange-red powder which dyes polyacrylonitrile fibres in fast reddish yellow shades.

The coupling component can be prepared by condensation of cyanoacetic acid-2-hydroxyethylamide with acetoacetic acid ester, for example in the presence of a secondary amine such as diethyl amine, morpholine, diethanolamine or piperidine.

EXAMPLE 137

22.1 Parts of 4-aminobenzoic acid-3'-dimethylamino-n-propylamide are dissolved in a mixture of 40 parts of 30% hydrochloric acid and 200 parts of water and diazotized at 0° with 6.9 parts of sodium nitrite. A solution of 18 parts of 1-methyl-2-keto-3-cyano-4-methyl-6-hydroxy-1,2-dihydropyridine and 120 parts of methyl alcohol is added dropwise to the ice-cold diazo solution. The pH of the reaction solution is then adjusted to 4.5 with sodium hydroxide and it is stirred continuously at 10° until the coupling reaction has run its course. The dye formed is isolated in the normal way and dried. It is applicable to polyacrylonitrile and polyvinylidene fibres, on which it gives greenish yellow dyeings of good light and wet fastness.

EXAMPLE 138

9.3 Parts of aminobenzene are dissolved in 200 parts of 6% hydrochloric acid at 0° and diazotized with 6.9 parts of sodium nitrite. To the ice-cold diazo solution is added over one hour an aqueous solution of 24 parts of 1-piperidyl-(4)-2-keto-3-cyano-4-methyl-6-hydroxy-1,2-dihydropyridine and 200 parts of water. The pH of the reaction solution is then adjusted to 5.5 by dropping in 10% sodium carbonate solution and it is stirred further at 0° until coupling is complete. The solution is then adjusted to a mineral acid reaction with hydrochloric acid and at 45° sodium chloride is added for precipitation. The dye settles out as the hydrochloride and is filtered off, washed with hydrochloric acid brine, dried and ground. It is obtained as a water soluble yellow powder which gives very fast yellow dyeings on polyacrylonitrile.

The coupling component employed in this Example can be prepared by condensing the reaction product of cyanoacetic acid methyl ester and 4-aminopiperidine with acetoacetic acid methyl ester.

EXAMPLE 139

99 Parts of cyanoacetic acid methyl ester are added dropwise to 102 parts of 3-amino-dimethylpropylamine so that the reaction temperature does not increase to above 40°. The mixture is then boiled with reflux, after which the temperature is allowed to decrease slightly and 116 parts of acetoacetic acid methyl ester and 7.1 parts of diethylamine are added. Boiling is continued for 3 hours with reflux. Then the methyl alcohol and the water of the reaction mixture are distilled off at reduced pressure. After cooling to 95°, the residue in the reaction vessel is diluted with 100 parts of water to a 52.5% aqueous solution of 1-(3'-dimethylamino)-propyl-2-keto-3-cyano-4-methyl-6-hydroxy-1,2-dihydropyridine. 50 Parts of this solution are dropped into an ice-cold aqueous diazo suspension prepared by the normal method with 24.8 parts of 1-aminobenzene-4-sulphonic acid phenylamide. The dye is isolated as the hydrochloride. On drying and grounding it is obtained as a water soluble yellow powder which dyes polyacrylonitrile and polyvinylidene fibres in very fast greenish yellow shades.

Dyes of comparably high quality can be arrived at by replacing the 102 parts of 3-aminodimethylpropylamine employed in the foregoing Example by the equivalent amount of one of the following amines:

2-dimethylaminoethylamine,
2-diethylaminoethylamine,
2-di-isopropylaminoethylamine,
3-diethylaminopropylamine-(1),
3-dibutylaminopropylamine,
2-dipropylaminoethylamine,
2-dibutylaminoethylamine,
4-dimethylaminobutylamine-(1),
4-diethylaminobutylamine-(3),
2-dimethylamino-tert.butylamine,
1,3-bis-(dimethylamino)-2-aminopropane,
1,3-bis-piperidino-2-aminopropane,
N-(2-aminoethyl)-N'-(methyl)-piperazine,
N-(2-aminoethyl)-piperazine,
N-(2-aminoethylmorpholine),
N-(3-aminopropyl)-morpholine,
4-dimethylaminobenzylamine,
4-diethylaminophenylethylamine,
4-amino-N,N-dimethylbenzylamine,
1-amino-3-diethylaminopropanol,
N-(2-hydroxyethyl)-ethylenediamine,
3-(2-dimethylaminoethoxy)-propylamine,
3-(2-dimethylaminoethylamino)-propylamine,
2-dihydroxyethylaminoethylamine,
2-dichloroethylaminoethylamine,
2'-aminoethylpyridine,
1-amino-4-methylpiperazine,
3-dihydroxyethylaminopropylamine,
1-(2'-aminoethylamino)-2-propanol, 2-(2'-aminoethyl)-1-methylpyrrolidine, Similar dyes of equally good quality can be produced by replacing the 24.8 parts of 1-aminobenzene-4-sulphonic acid phenylamide used in the preceding Example by the equivalent amount of one of the following 4-aminobenzoic acid ethylester,
4-aminobenzoic acid phenylamide,
2-aminobenzoic acid methylester,
1-amino-2-nitro-4-methylbenzene,
1-amino-2,5-dichlorobenzene,
4-aminodiphenyl,
2-aminodiphenyl,
2-amino-4-chlorodiphenylether,
4-amino-4'-chlorodiphenylether,
1-amino-4-methylbenzene-3-sulphonic acid phenylamide,
2-aminobenzene-1-sulphonic acid N-ethyl-N-phenylamide,
1-amino-3-benzoylaminobenzene,
1-amino-3-chloro-4-methoxybenzene,
4-amino-2',4'-dinitrodiphenylamine,
1-amino-4-methylbenzene,
1-amino-2-methyl-4-chlorobenzene,
1-amino-2-chlorobenzene,
1-amino-2-cyano-4-chlorobenzene,
1-amino-2-chloro-4-nitrobenzene,
1-amino-2-methoxy-4-nitrobenzene,
1-amino-4-benzoylaminobenzene,
4-aminobenzenesulphonic acid dimethylamide,
1-amino-2-methyl-5-nitrobenzene,
1-amino-4-carbethoxybenzene,
4-aminoazobenzene,
4-amino-4'-methylbenzophenone.

EXAMPLE 140

25.6 Parts of 4-amino-4'-chlorodiphenylether-chlorohydrate are dissolved in 300 parts of water and after the addition of 18 parts of 30% hydrochloric acid are diazotized by the normal method with 6.9 parts of sodium nitrite. The diazo solution is added to a solution of 24.7 parts of 1-(3'-N',N'-dimethylaminopropyl)-2-keto-3-cyano-4-methyl-6-hydroxy-1,2-dihydropyridine and 200 parts of 2% aqueous hydrochloric acid at 10°, with continuous stirring to the end-point of the coupling reaction. The dye formed is salted out at 50° with sodium chloride, filtered off and dried. This new dye is an orange powder which gives bright reddish yellow shades of high light and wet fastness on polyacrylonitrile fibres.

The coupling component is prepared by condensation of cyanoacetic acid-3-dimethylamino-n-propylamide with acetoacetic acid ethyl ester.

The following Examples may be produced as indicated in one of the Examples 1 to 140 and/or are the formulae of representative dyes of the said foregoing Examples:

Example 141

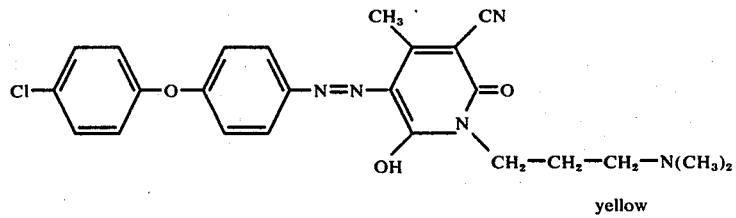

yellow

Example 142

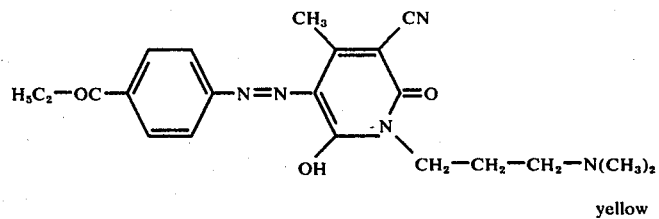

yellow

Example 143

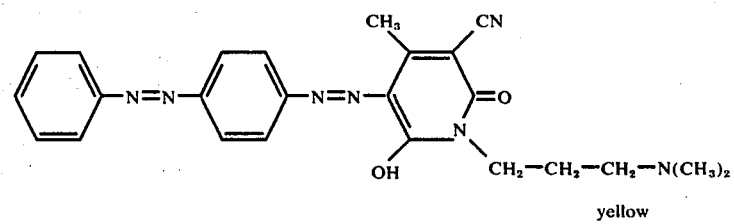

yellow

Example 144

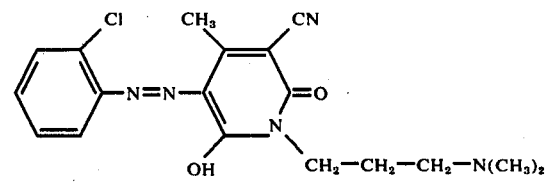

yellow

Example 145

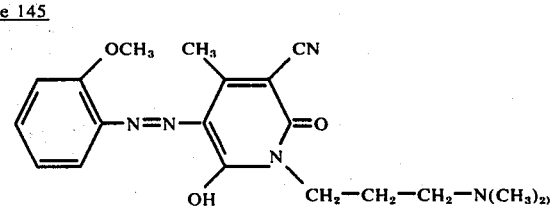

yellow

Example 146

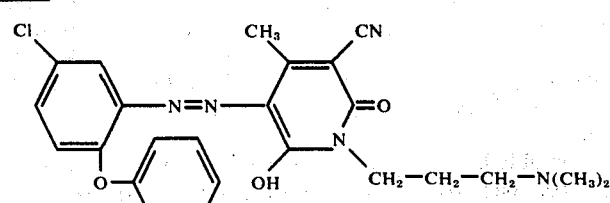

yellow

Example 147

-continued

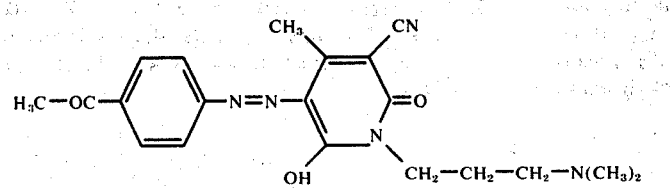

yellow

What is claimed is:
1. A compound of the formula

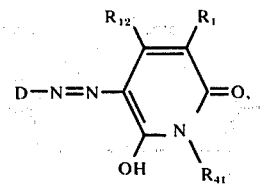

wherein
D is carbocyclic aryl, substituted carbocyclic aryl, heterocyclic aryl or substituted heterocyclic aryl, wherein carbocyclic aryl is phenyl, naphthyl or tetrahydronaphthyl, heterocyclic aryl is pyridyl, quinolyl, tetrahydroquinolyl, 1,2,4-triazolonyl, 1,2,4-triazolyl, indazolyl, thiadiazolyl, thiazolyl or benzothiazolyl, each substituent of substituted carbocyclic aryl and substituted heterocyclic aryl is independently halo, nitro, cyano, thiocyano, hydroxy, alkyl, alkoxy, trifluoroalkyl, trichloroalkyl, phenyl, phenoxy, chlorophenoxy, $NH_2$, alkylamino, dialkylamino, anilino, 2,4-dinitroanilino, alkylcarbonyl, alkoxycarbonyl, alkylcabonylamino, benzamido, alkylbenzoyl, phenylcarbamoyl, sulfamoyl, dialkylsulfamoyl, N-alkyl-N-phenylsulfamoyl, phenylsulfamoyl, phenylazo, diphenylazo or naphthylazo,
$R_1$ is hydrogen or cyano,
$R_{12}$ is alkyl, phenyl or benzyl, and
$R_{41}$ is

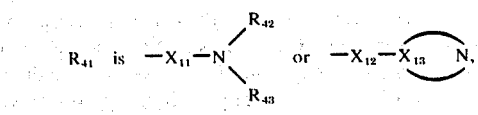

wherein each of $R_{42}$ and $R_{43}$ is independently hydrogen, alkyl, substituted alkyl, cyclohexyl, alkylcyclohexyl, carbocyclic aryl or substituted carbocyclic aryl, wherein each substituent of substituted alkyl is independently hydroxy, chloro or cyano, each carbocyclic aryl is independently phenyl, naphthyl or tetrahydronaphthyl, and each substituent of each substituted carbocyclic aryl is independently halo, nitro, cyano, thiocyano, hydroxy, alkyl, alkoxy, trifluoroalkyl, trichloroalkyl, phenyl, phenoxy, $NH_2$, alkylamino, dialkylamino, anilino, alkylsulfonyl, phenylsulfonyl, naphthylsulfonyl, tetrahydronapthylsulfonyl, sulfamoyl, alkylsulfamoyl, dialkylsulfamoyl, phenylsulfamoyl, naphthylsulfamoyl, tetrahydronaphthylsulfamoyl, phenylazo, diphenylazo or naphthylazo, or
$R_{42}$ and $R_{43}$ taken together and with the nitrogen atom to which they are joined are piperidino, pyrrolidino, morpholino, aziridino, piperazino, N'-alkylpiperazino or N'-alkylsulfonylpiperazino,
$X_{11}$ is —Alk—, —Z—Alk—, —Alk—Z— or —Alk'—Z—Alk', wherein Alk is straight or branched chain alkylene of 1 to 12 carbon atoms or straight or branched chain alkylene of 1 to 12 carbon atoms substituted by halo, hydroxy, cyano, phenyl, dimethylamino or piperidino, each —Alk'— is independently straight or branched chain alkylene or straight or branched chain alkylene substituted by halo, hydroxy, cyano, phenyl, dimethylamino or piperidino with the proviso that the two Alk' radicals together contain 2 to 12 carbon atoms, and Z is

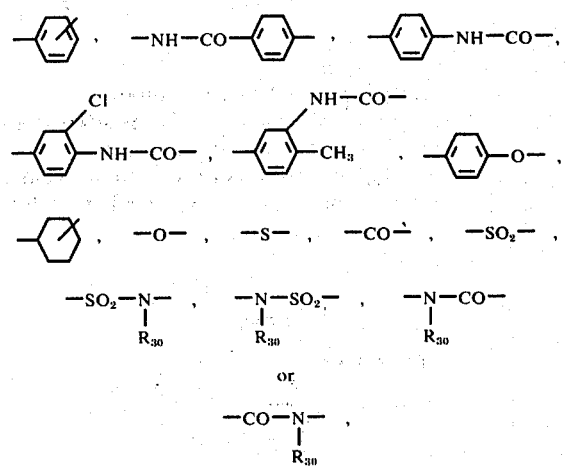

wherein $R_{30}$ is hydrogen, alkyl, substituted alkyl, cyclohexyl, alkylcyclohexyl, carbocyclic aryl or substituted carbocyclic aryl wherein each substituent of substituted alkyl is independently chloro, hydroxy or cyano, each carbocyclic aryl is independently phenyl, naphthyl or tetrahydronaphthyl, and each substituent of substituted carbocyclic aryl is independently halo, nitro, cyano, thiocyano, hydroxy, alkoxy, alkyl, trifluoroakyl, trichloroalkyl, phenyl, phenoxy, $NH_2$, alkylamino, dialkylamino, anilino, phenylazo, diphenylazo or naphthylazo,
$X_{12}$ is a direct link or $X_{11}$,
$X_{13}$ is nitrogen or carbon, and

is amidino, pyridyl, alkylpyridyl, piperidyl, pyrrolidyl, alkylpyrrolidyl, morpholinyl, aziridyl, piperazinyl or pyrazolinyl,
wherein each alkyl, trifluoroalkyl, trichloroalkyl, alkylamino, alkylsulfonyl, alkylsulfamoyl and each alkyl chain of each dialkylamino, alkylcarbonyl, alkylcarbonylamino, alkylbenzoyl, dialkylsulfamoyl, N-alkyl-N-phenylsulfamoyl, substituted alkyl, alkylcyclohexyl, N'-alkylpiperazino, N'-alkylsulfonylpiperazino, alkylpyrrolidinyl and alkylpyridyl independently has 1 to 12 carbon atoms, each alkoxy and alkoxy chain of alkoxycarbonyl independently has 1 to 6 carbon atoms, and each halo is independently fluoro, chloro or bromo.

2. A compound according to claim 1 having the formula

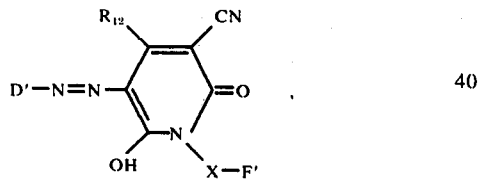

wherein

D' is phenyl, substituted phenyl, thiazolyl, 1,2,4-triazolonyl, lower alkyl-1,2,4-triazolyl, indazolyl, lower alkylindiazolyl, 1,3,4-thiadiazolyl, lower alkyl-1,3,4-thiadiazolyl or lower alkylsulfonylbenzothiazolyl, wherein each substituent of substituted phenyl is independently chloro, bromo, nitro, cyano, lower alkyl, phenyl, lower alkoxy, phenoxy, 4-chlorophenoxy, lower alkylcarbonyl, lower alkoxycarbonyl, lower alkylcarbonylamino, benzamido, 4-methylbenzoyl, phenylcarbamoyl, sulfamoyl, dilower alkylsulfamoyl, N-lower alkyl-N-phenylsulfamoyl, phenylsulfamoyl, phenylazo or 2,4-dinitroanilino, $R_{12}$ is lower alkyl, phenyl or benzyl, X is —Alk—, —Alk—Z—Alk—, —Z—Alk— or —Alk—Z—, wherein each -Alk- is independently straight or branched chain lower alkylene and Z is —O—,

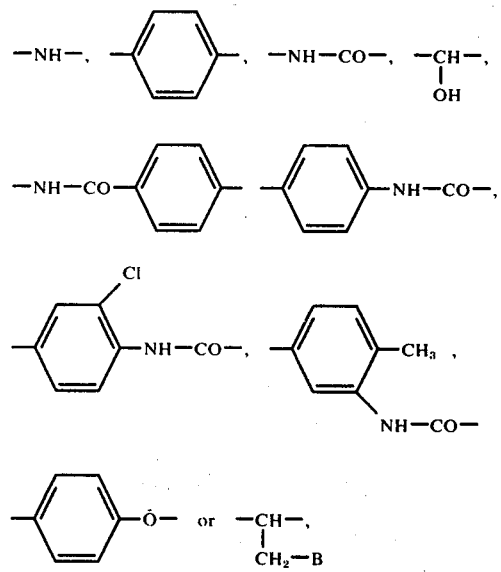

wherein B is N,N-diloweralkylamino or piperidino, and

F' is $NH_2$, monosubstituted amino, disubstituted amino, morpholino, piperidino, piperazino, N'-lower alkylpiperazino, N'-lower alkylsulfonylpiperazino, 2-(N-lower alkylpyrrolidyl), amidino, 2-pyridyl, 4-pyridyl or 3-(4-lower alkylpyridyl), wherein each substituent of monosubstituted amino and disubstituted amino is independently lower alkyl, lower hydroxyalkyl, lower dihydroxyalkyl, lower cyanoalkyl or lower chloroalkyl.

3. A compound according to claim 2 wherein

D' is phenyl, substituted phenyl, thiazolyl, 1,2,4-triazolonyl, methyl-1,2,4-triazolyl, indazolyl, methylindazolyl, 1,3,4-thiadiazolyl, methyl-1,3,4-thiadiazolyl or methylsulfonylbenzothiazolyl, wherein each substituent of substituted phenyl is independently methyl, methoxy, ethoxy, chloro, bromo, nitro, cyano, phenyl, phenoxy, 4-chlorophenoxy, acetyl, propionyl, methoxycarbonyl, ethoxycarbonyl, 4-methylbenzoyl, phenylcarbamoyl, sulfamoyl, dimethylsulfamoyl, N-ethyl-N-phenylsulfamoyl, phenylsulfamoyl, acetamido, benzamido, phenylazo or 2,4-dinitroanilino, $R_{12}$ is methyl, ethyl, phenyl or benzyl, and X is —$CH_2CH_2$—, —$CH_2CH_2CH_2$—,

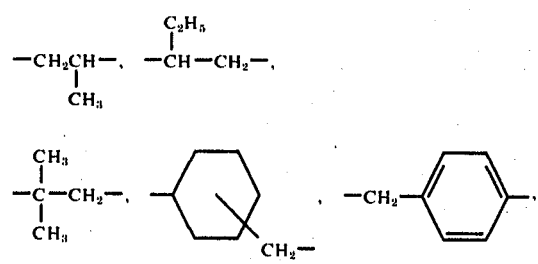

-continued
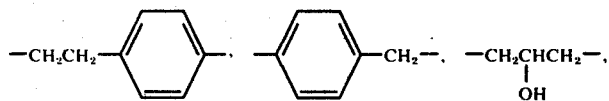
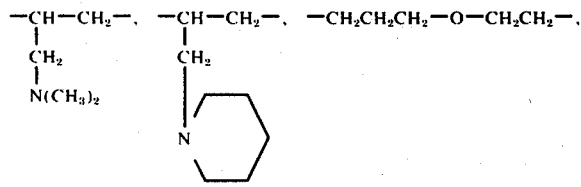
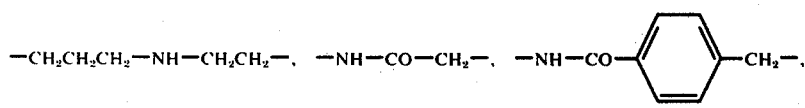
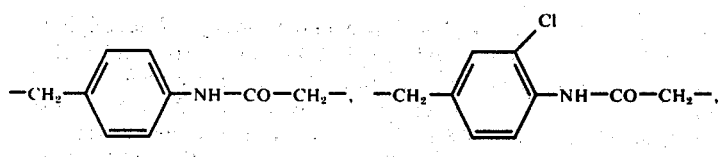
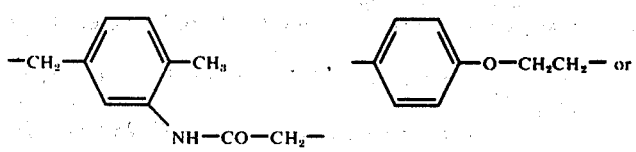
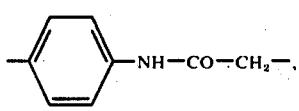
and

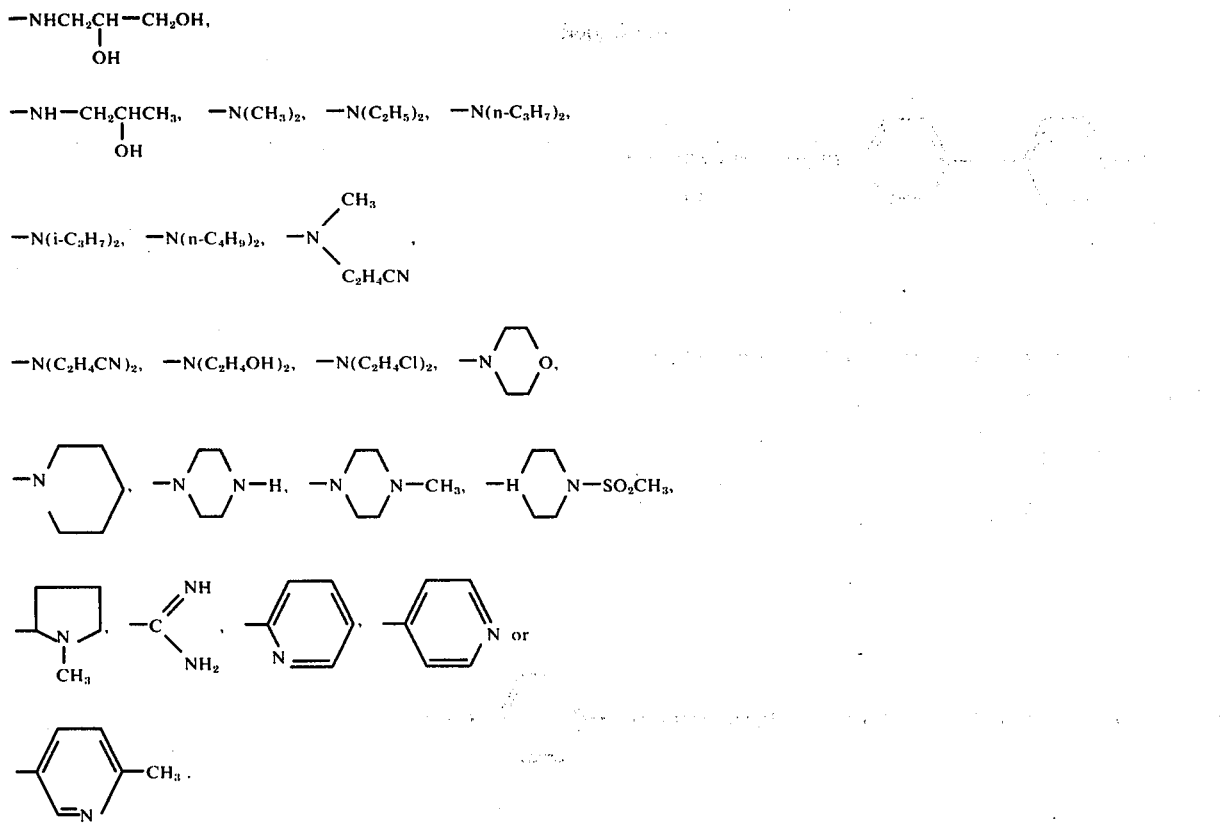

4. A compound according to claim 3 wherein D' is phenyl or substituted phenyl having 1 to 3 substituents.

5. A compound according to claim 4 wherein D' is phenyl, 2-methylphenyl, 3-methylphenyl, 4-methylphenyl, 2,5-dimethylphenyl, 2-methoxyphenyl, 4-methoxyphenyl, 4-ethoxyphenyl, 2-chlorophenyl, 3-chlorophenyl, 4-chlorophenyl, 2,5-dichlorophenyl, 3,4-dichlorophenyl, 2,4,5-trichlorophenyl, 2,4,6-trichlorophenyl, 2-bromophenyl, 3-bromophenyl, 2,4,6-tribromophenyl, 3-chloro-4-methoxyphenyl, 2-methyl-4-chlorophenyl, 3-nitrophenyl, 4-nitrophenyl, 2,4-dinitrophenyl, 2-nitro-4-methylphenyl, 2-methyl-5-nitrophenyl, 2-nitro-4-chlorophenyl, 3-nitro-4-chlorophenyl, 2-chloro-4-nitrophenyl, 2,6-dichloro-4-nitrophenyl, 2-methoxy-4-nitrophenyl, 2-methoxy-5-nitrophenyl, 2-cyano-4-chlorophenyl, 2-phenylphenyl, 4-phenylphenyl, 3-chloro-6-phenoxyphenyl, 4-(4'-chlorophenoxy)phenyl, 4-acetylphenyl, 4-propionylphenyl, 2-methoxycarbonylphenyl, 4-ethoxycarbonylphenyl, 4-(4'-methylbenzoyl)-phenyl, 4-phenylcarbamoylphenyl, 2-methoxy-5-sulfamoylphenyl, 4-N,N-dimethylsulfamoylphenyl, 4-N-phenylsulfamoylphenyl, 2-N-ethyl-N-phenylsulfamoylphenyl, 3-phenylsulfamoyl-4-methylphenyl, 4-acetamidophenyl, 3-benzamidophenyl, 4-benzamidophenyl, 4-phenylazophenyl or 4-(2,4-dinitroanilino)-phenyl.

6. A compound according to claim 1 wherein $R_1$ is cyano.

7. A compound according to claim 1 wherein $R_{12}$ is alkyl or phenyl.

8. A compound according to claim 7 wherein $R_1$ is cyano.

9. The compound according to claim 8 having the formula

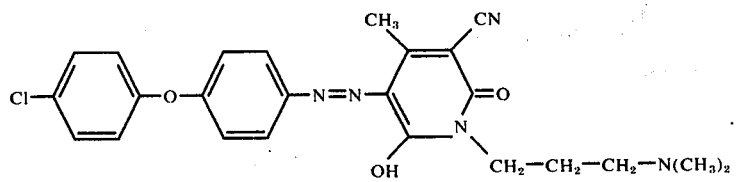

10. The compound according to claim 8 having the formula

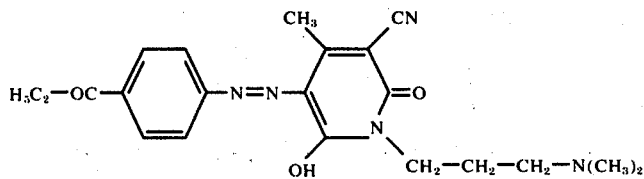
11. The compound according to claim 8 having the formula
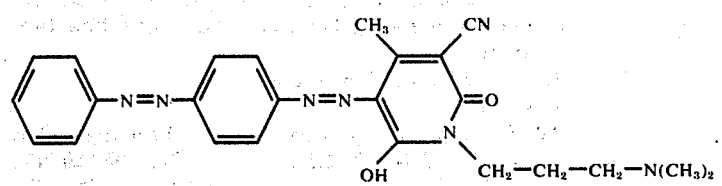
12. The compound according to claim 8 having the formula
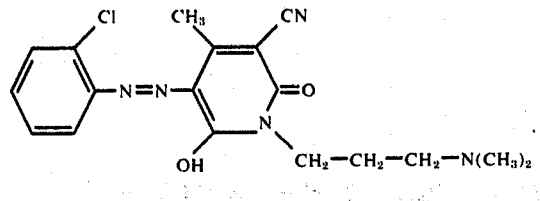
13. The compound according to claim 8 having the formula
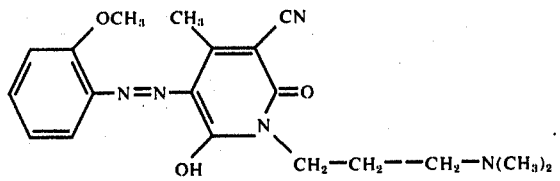
14. The compound according to claim 8 having the formula
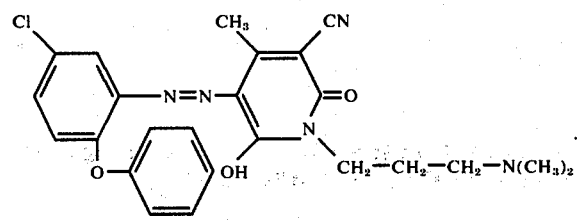
15. The compound according to claim 8 having the formula
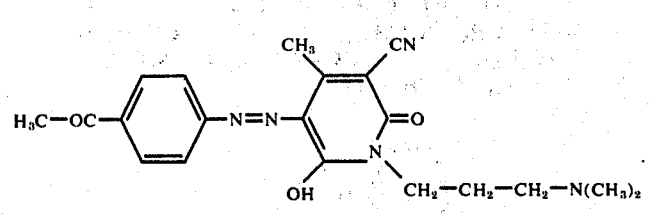
16. The compound according to claim 8 having the formula

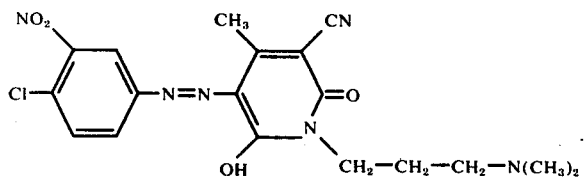

17. A compound of formula

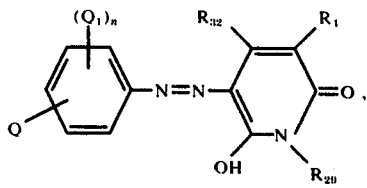

wherein

Q is —CO—NH—C$_2$H$_4$—N(CH$_3$)$_2$, —CO—N-H—CH$_2$CH$_2$CH$_2$N(CH$_3$)$_2$, —CO—N(CH$_3$)—C$_2$-H$_4$—N(CH$_3$)$_2$, —CO—CH$_2$—N(CH$_3$)$_2$,

—CO—CH$_2$—N(C$_2$H$_4$OH)$_2$, —CO—CH$_2$—N⟨pyrrolidine⟩,

—CO—CH—N(CH$_3$)$_2$, —CO—C$_2$H$_4$—N(CH$_3$)C$_2$H$_4$OH,
     |
   CH$_3$

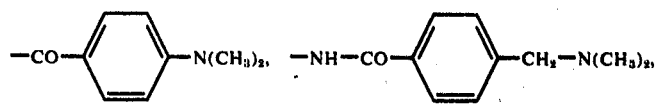

—NH—CO—NH—C$_2$H$_4$—N(CH$_3$)$_2$, —N-H—CO—CH$_2$—N(CH$_3$)$_2$, —NH—CO—CH-$_2$—N(C$_2$H$_5$)$_2$, —NH—CO—C$_2$H$_4$—N(CH$_3$)$_2$, —O—C$_2$H$_4$—N(CH$_3$)$_2$ or

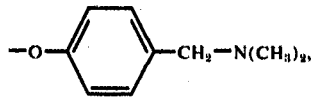

Q$_1$ is chloro, bromo, methyl, ethyl, methoxy, ethoxy or phenoxy,

R$_1$ is hydrogen or cyano,

R$_{29}$ is methyl, ethyl, cyclohexyl, phenyl, benzyl, 3-methoxypropyl, 3-N,N-dimethylaminopropyl, 2-morpholinoethyl, 2-(2-pyridyl)ethyl, 4-(2-N,N-dimethylaminoethyl)phenyl, NH$_2$ or dimethylamino, R$_{32}$ is methyl or phenyl, and n is 0 or 1.

18. A compound according to claim 17 wherein Q is —CO—NH—C$_2$H$_4$—N(CH$_3$)$_2$, —CO—N(CH$_3$)C$_2$-H$_4$—N(CH$_3$)$_2$, —CO—CH$_2$—N(C$_2$H$_4$OH)$_2$, —CO—C$_2$-H$_4$—N(CH$_3$)C$_2$H$_4$OH,

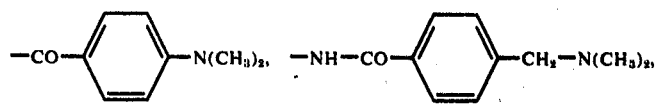

—NH—CO—NH—C$_2$H$_4$—N(CH$_3$)$_2$, —N-H—CO—CH$_2$—N(CH$_3$)$_2$, —NH—CO—C$_2$-H$_4$—N(CH$_3$)$_2$, —O—C$_2$H$_4$—N(CH$_3$)$_2$ or

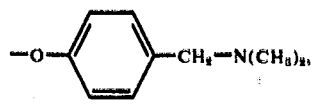

Q$_1$ is chloro, bromo, methyl, ethyl, methoxy, ethoxy or phenoxy,

R$_1$ is hydrogen or cyano,

R$_{29}$ is methyl, ethyl, phenyl or cyclohexyl,

R$_{32}$ is methyl, and n is 0 or 1.

* * * * *